(12) United States Patent
Heinrich

(10) Patent No.: US 7,517,356 B2
(45) Date of Patent: Apr. 14, 2009

(54) SURGICAL STAPLER AND METHOD

(75) Inventor: Russell Heinrich, Madison, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 563 days.

(21) Appl. No.: 10/510,451

(22) PCT Filed: Apr. 16, 2003

(86) PCT No.: PCT/US03/11778

§ 371 (c)(1),
(2), (4) Date: Oct. 4, 2004

(87) PCT Pub. No.: WO03/088845

PCT Pub. Date: Oct. 30, 2003

(65) Prior Publication Data

US 2005/0184121 A1 Aug. 25, 2005

Related U.S. Application Data

(60) Provisional application No. 60/373,224, filed on Apr. 16, 2002.

(51) Int. Cl.
*A61B 17/08* (2006.01)
(52) U.S. Cl. .................. 606/219; 227/176.1; 227/178.1; 227/180.1
(58) Field of Classification Search ............... 606/219, 606/139, 142, 143
See application file for complete search history.

(56) References Cited

U.S. PATENT DOCUMENTS

| 4,573,468 | A | 3/1986 | Conta et al. |
| 4,672,969 | A | 6/1987 | Dew |
| 5,385,606 | A | 1/1995 | Kowanko |
| 5,403,312 | A | 4/1995 | Yates et al. |
| 5,415,159 | A | 5/1995 | Ortiz et al. |
| 5,417,687 | A | 5/1995 | Nardella et al. |
| 5,531,744 | A | 7/1996 | Nardella et al. |
| 5,582,834 | A | 12/1996 | Leung et al. |
| 5,599,350 | A | 2/1997 | Schulze et al. |
| 5,624,452 | A | 4/1997 | Yates |
| 5,658,279 | A | 8/1997 | Nardella et al. |
| 5,669,934 | A | 9/1997 | Sawyer |
| 5,688,270 | A | 11/1997 | Yates et al. |

(Continued)

FOREIGN PATENT DOCUMENTS

EP 0 577 373 1/1994

(Continued)

*Primary Examiner*—Michael J. Hayes
*Assistant Examiner*—Michael G. Mendoza

(57) ABSTRACT

The present disclosure relates to surgical instruments including a staple anvil formed in a distal end of the surgical stapler and a staple cartridge selectively receivable in a distal end of the surgical stapler and in juxtaposition relative to the staple anvil, the staple cartridge including one or more laterally spaced apart rows of staple slots formed in an upper surface thereof, a plurality of surgical staples disposed, one each, within the staple slots, and a staple line reinforcing system configured and adapted to augment the strength of the staple line formed by the firing of the surgical staples into body tissue, wherein the surgical stapler concomitantly drives the plurality of surgical staples through the adjacent layers of body tissue to mechanically secure the body tissue and activates the reinforcing system to non-mechanically secure the adjacent layers of body tissue to one another.

47 Claims, 12 Drawing Sheets

U.S. PATENT DOCUMENTS

| | | | |
|---|---|---|---|
| 5,693,051 A | 12/1997 | Schulze et al. | |
| 5,709,680 A | 1/1998 | Yates et al. | |
| 5,716,366 A | 2/1998 | Yates | |
| 5,735,848 A | 4/1998 | Yates et al. | |
| 5,755,717 A | 5/1998 | Yates et al. | |
| 5,799,857 A | 9/1998 | Robertson et al. | |
| 5,807,393 A | 9/1998 | Williamson, IV et al. | |
| 5,810,811 A | 9/1998 | Yates et al. | |
| 5,817,091 A | 10/1998 | Nardella et al. | |
| 5,817,093 A | 10/1998 | Williamson, IV et al. | |
| 5,833,690 A | 11/1998 | Yates et al. | |
| 5,876,401 A | 3/1999 | Schulze et al. | |
| 5,895,412 A * | 4/1999 | Tucker | 606/215 |
| 5,897,562 A * | 4/1999 | Bolanos et al. | 606/139 |
| 5,915,616 A | 6/1999 | Viola et al. | |
| 5,964,394 A | 10/1999 | Robertson | |
| 6,003,517 A | 12/1999 | Sheffield et al. | |
| 6,024,741 A | 2/2000 | Williamson, IV et al. | |
| 6,032,849 A | 3/2000 | Mastri et al. | |
| 6,045,560 A | 4/2000 | McKean et al. | |
| H1904 H | 10/2000 | Yates et al. | |
| 6,165,175 A | 12/2000 | Wampler et al. | |
| 6,239,190 B1 | 5/2001 | Wilkinson et al. | |
| 6,241,139 B1 | 6/2001 | Milliman et al. | |
| 6,250,532 B1 | 6/2001 | Green et al. | |
| 6,296,640 B1 | 10/2001 | Wampler et al. | |
| 6,330,965 B1 | 12/2001 | Milliman et al. | |
| 6,468,275 B1 | 10/2002 | Wampler et al. | |
| 6,485,490 B2 | 11/2002 | Wampler et al. | |
| 6,488,197 B1 * | 12/2002 | Whitman | 227/180.1 |
| 6,491,201 B1 | 12/2002 | Whitman | |
| 6,681,979 B2 | 1/2004 | Whitman | |
| 6,695,199 B2 | 2/2004 | Whitman | |
| 7,238,195 B2 * | 7/2007 | Viola | 606/219 |
| 2001/0007069 A1 | 7/2001 | Bombard et al. | |
| 2002/0156150 A1 | 10/2002 | Williams | |
| 2002/0165562 A1 | 11/2002 | Grant et al. | |
| 2002/0173558 A1 | 11/2002 | Williams et al. | |
| 2003/0050590 A1 | 3/2003 | Kirsch | |
| 2003/0073982 A1 | 4/2003 | Whitman | |
| 2003/0089757 A1 | 5/2003 | Whitman | |
| 2004/0093029 A1 | 5/2004 | Zubik et al. | |

FOREIGN PATENT DOCUMENTS

| | | |
|---|---|---|
| WO | WO 00/56376 | 9/2000 |
| WO | WO 01/62158 | 8/2001 |
| WO | WO 01/62162 | 8/2001 |
| WO | WO 02/30297 | 4/2002 |
| WO | WO 03/088844 | 10/2003 |
| WO | WO 03/094743 | 11/2003 |
| WO | WO 03/094746 | 11/2003 |
| WO | WO 03/105698 | 12/2003 |

* cited by examiner

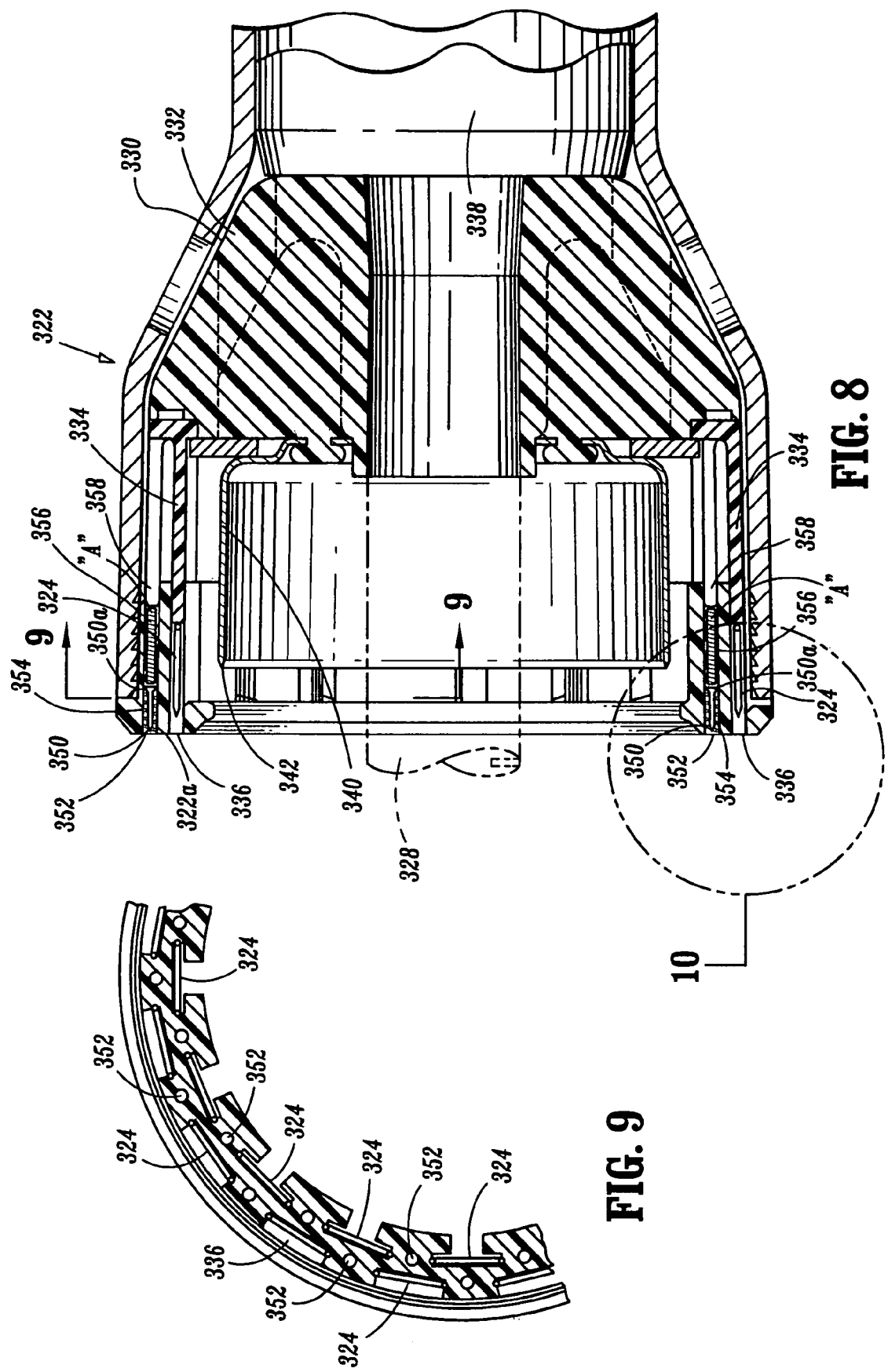

SURGICAL STAPLER AND METHOD

CROSS REFERENCE TO RELATED APPLICATIONS

This is a National Stage Application of PCT/US 03/11778 under 35 USC §371(a), which claims priority of U.S. Provisional Patent Application Ser. No. 60/373,224 filed Apr. 16, 2002, the entire contents of which are hereby incorporated by reference.

BACKGROUND

1. Technical Field

The present disclosure relates to surgical instruments and methods for enhancing properties of tissue repaired or joined by surgical staples and, more particularly to surgical instruments configured to apply surgical mechanical fasteners concomitantly with a non-mechanical biocompatible wound closure material to enhance the properties of repaired or adjoined tissue at a target surgical site.

2. Discussion of Related Art

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples, as will be discussed below. The intended function of sutures is to hold the edges of a wound or tissue against one another during the healing process so as to reduce discomfort, pain, scarring and the time required for healing.

Recently, many procedures which in the past required conventional suturing have been replaced by staple suturing which involves the application of the staples to the edges of the wound or tissue with the use of a surgical stapler. Surgical staplers have been developed for joining adjacent tissue, for providing hemostasis of adjacent tissue and for providing hemostasis in conjunction with cutting of adjacent tissue. Such surgical staplers include both linear and annular type configurations. A typical linear stapler and cutter includes parallel rows of staples with a slot for a cutting means to travel between the rows of staples. Typical linear type staplers are disclosed in commonly assigned U.S. Pat. No. 6,045,560 to McKean et al., U.S. Pat. No. 6,032,849 to Mastri et al., and U.S. Pat. No. 5,964,394 to Robertson, the entire contents of each of which are incorporated herein by reference. A typical annular stapler and cutter, including a plurality of annular rows of staples, typically two, and an annular blade disposed internal of the rows of staples, is disclosed in commonly assigned U.S. Pat. Nos. 5,799,857 and 5,915,616 to Robertson et al., the entire contents of each of which are incorporated herein by reference. These types of surgical staplers secure adjoining body tissue for improved cutting, join layers of tissue to one another and provide hemostasis by applying parallel or annular rows of staples to surrounding tissue as the cutting means cuts between the parallel or annular rows. Accordingly, by enabling a surgeon to perform all of these tasks simultaneously, surgical staplers have been effective in decreasing the amount of time it takes to fasten tissue together. To even further enhance joining and hemostasis in instances where the stapler is used in highly vascularized tissue, surgical staplers with multiple rows of staples have been used with a high degree of success.

Another procedure which has been developed includes the use of energy for welding or otherwise joining or connecting biological tissue. For example, RF (radio-frequency) energy has recently been utilized in both uni- and bi-polar generators to attempt to "weld" or "solder" biological tissue. Uni-polar devices utilize one electrode associated with a cutting or cauterizing instrument and a remote return electrode, usually adhered externally to the patient. Bi-polar devices involve the use of an instrument having two electrodes wherein the cauterizing current is generally limited to tissue solely between two electrodes of the instrument.

Use of energy to effect wound closure or other reconstruction of biological tissue involves the application of energy to produce thermal heating of the biological tissue to degrees suitable for denaturing the tissue proteins such that the collagenous elements of the tissue form "biological glue" which seals the tissue to effect the joining. This glue is later reabsorbed by the body during the healing process.

In addition, biological tissue adhesives have recently been developed for tissue repair and the creation of anastomoses. Generally, biological adhesives bond separated tissues together to aid in the healing process and to enhance the tissue strength. Such adhesives may be used instead of suturing and stapling for example in surgical procedures for the repair of tissue or the creation of anastomoses.

The application of a suitable biocompatible adhesive offers many advantages to the patient and the surgeon alike such as, for example, the avoidance of penetration of tissue by needles and/or staples, as well as the immediate sealing of the tissue being treated. Moreover, use of a biocompatible adhesive tends to minimize foreign body reaction and scarring. Despite these advantages, however, the weakness along the tissue seam remains as a primary disadvantage in the use of biocompatible adhesives.

Therefore, there is a need for surgical stapler instruments, for example surgical fasteners or staplers which reduce the trauma suffered by a patient, reduce the number of gaps between or at individual staple sites, reduce leakage of fluids, reduce bleeding, and/or which create a relatively strong bond between adjacent body tissues, e.g., along staple lines and tissue seams.

SUMMARY

The present disclosure relates to surgical instruments and methods for enhancing the properties of tissue to be repaired or joined.

According to one aspect of the present disclosure a method for enhancing one or more properties of body tissue to be repaired or joined by surgical staples includes the step of providing a surgical stapler including a staple anvil and a staple cartridge each positioned adjacent a distal end of the surgical stapler and operable in juxtaposition relative to each other. The staple cartridge includes a working surface, one or more rows of individual staple slots formed in the working surface, a plurality of surgical staples individually disposed within the individual staple slots, a driving member for firing the surgical staples from their slots and against the staple anvil, a body tissue property enhancing system configured and adapted to enhance one or more properties of the body tissue to be repaired or joined by the surgical staples formed by firing them into body tissue, the body tissue property enhancing system including a reservoir of biocompatible wound closure material and a plurality of ducts in communication with the reservoir and the working surface of the cartridge, and a plurality of deployable needles each having a tip, the needles being adapted and disposed in the ducts such that the tips can be extended out of the working surface of the staple cartridge to penetrate at least a layer of adjacent layers of body tissue and to allow the biocompatible wound closure material to be delivered along the exterior of the needles to penetrate one or more layers of body tissue.

The method further includes the steps approximating the staple anvil and staple cartridge with adjacent layers of body tissue therebetween, and firing the surgical stapler, wherein firing of the surgical stapler includes driving the plurality of surgical staples through the adjacent layers of body tissue to mechanically secure the layers of body tissue together and concomitantly activating the body tissue enhancing system to enhance one or more properties of the adjacent layers of repaired or joined body tissue.

It is envisioned that the activating of the body tissue property enhancing system includes delivering an amount of the biocompatible wound closure material to at least one of or between the adjacent layers of repaired or joined body tissue. Upon firing of the surgical stapler, the biocompatible wound closure material is expelled from the reservoir of the staple cartridge.

It is further envisioned that in the providing step each of the plurality of deployable needles is normally biased to a non-extended position and is movable against the bias to the extended position.

The activating of the body tissue property enhancing system includes delivering an amount of energy to at least one of or between the adjacent layers of body tissue to cauterize at least one of or the adjacent layers of body tissue.

The plurality of deployable needles are adapted to deliver the amount of energy to at least a layer of the body tissue to cauterize the body tissue.

The biocompatible wound closure material is an adhesive material. It is contemplated that the adhesive material is made of a protein derived, aldehyde based adhesive material. Alternatively, it is contemplated that the adhesive material is made of an albumin/glutaraldehyde material. The adhesive material can be a cyanoacrylate-based material.

It is envisioned that the biocompatible wound closure material is a tissue sealant material, wherein the tissue sealant material is made of a synthetic polyethylene glycol-based hydrogel material.

It is further envisioned that the biocompatible wound closure material is a hemostat, wherein the hemostat is made of a combination of fibrinogen and thrombin.

According to another aspect of the present disclosure, a surgical stapler is provided and includes a first jaw adapted to receive a staple cartridge in a distal end of the first jaw, the staple cartridge containing a plurality of individual surgical staples, and having a working surface with a plurality of staple slots formed therein, a second jaw: having a staple anvil in a distal end of the second jaw, such that during the operation of the surgical stapler the staple cartridge and the staple anvil can be approximated relative to one another, a driving member for firing the surgical staples from their staple slots and against the approximated staple anvil, and a body tissue property enhancing system for enhancing one or more properties of body tissue to be repaired or joined by the surgical stapler. The body tissue property enhancing system includes a biocompatible wound closure material dispensing system for dispensing an amount of surgically biocompatible wound closure material to a target staple site during at least one of prior to, after and concomitant with a firing of the surgical stapler to expel the plurality of staples loaded in the staple cartridge, the body tissue property enhancing system comprising at least one reservoir disposed in the staple cartridge for containing the biocompatible wound closure material therein, a plurality of ducts formed in the staple cartridge, wherein the plurality of ducts communicate with and extend from the at least one adhesive reservoir to the working surface of the staple cartridge, and a plurality of deployable needles each having a tip, the needles being adapted and disposed in the ducts of the staple cartridge such that their tips can be extended out of the working surface of the staple cartridge to penetrate at least a layer of the adjacent layers of body tissue and to allow the biocompatible wound closure material to be delivered along the exterior of the needles to penetrate one or more layers of the body tissue.

The first jaw is adapted to receive a drive member adapted to be slidingly disposed within the staple cartridge, the drive member being adapted to force the biocompatible wound closure material from the reservoir out through the plurality of ducts and about the needles disposed therein as the drive member is displaced in a distal direction, to allow the biocompatible wound closure material to penetrate into the body tissue to be repaired or joined.

The staple cartridge can further include one or more laterally spaced rows of individual staple slots, the rows of staple slots extending along the staple cartridge, a plurality of individual surgical staples having a back span and disposed, one each, within the individual staple slots, and a plurality of staple pushers disposed one each within the staple slots and in a position to push one of the plurality of staples from the slot, wherein the drive member is adapted to displace the staple pushers into the slots and to concomitantly expel a quantity of the biocompatible wound closure material about the needles and out through the plurality of ducts.

The biocompatible wound closure material dispensing system further includes a flexible liner extending longitudinally through the staple cartridge, wherein the liner prevents the biocompatible wound closure material from contacting the drive member as the drive member is displaced distally through the staple cartridge.

The plurality of needles have a tip, a first position wherein the needles are entirely retained within the staple cartridge and a second position wherein the tips of the plurality of needles project out from the working surface of the staple cartridge. Each of the plurality of needles is preferably biased to the first position.

The surgical stapler can be for performing an open gastrointestinal anastomosis operations, an endoscopic or laparoscopic gastrointestinal operations, and an end-to-end anastomosis operations.

The biocompatible wound closure material is an adhesive made of a protein derived, aldehyde-based adhesive material, an albumin/glutaraldehyde material, or a cyanoacrylate-based material. The biocompatible wound closure material can be a tissue sealant material, wherein the tissue sealant material is made of a synthetic polyethylene glycol-based hydrogel material. The biocompatible wound closure material can be a hemostat.

The plurality of ducts are preferably positioned adjacent to or aligned between the one or more laterally spaced apart rows of staple slots. Each of the plurality of deployable needles is provided with a retracting element for withdrawing each of the plurality of deployable needles back into the staple cartridge after a firing of the surgical stapler.

According to a further aspect of the present disclosure, a surgical stapler is provided and includes a first jaw adapted to receive a staple cartridge in a distal end of the first jaw, the staple cartridge containing a plurality of individual surgical staples, and a working surface with a plurality of staple slots formed therein, a second jaw having a staple anvil in a distal end of the second jaw, such that during the operation of the surgical stapler the staple cartridge and the staple anvil can be approximated relative to each other, a driving member for firing the surgical staples from the staple slots and against the approximated staple anvil, and a tissue cauterizing system operatively associated with the staple cartridge for enhancing one or more properties of adjacent layers of body tissue to be repaired or joined by the surgical stapler, the tissue cauterizing system including a plurality of deployable needles each having a tip, the needles being adapted and disposed in the cartridge such that their tips can be extended out of the working surface of the staple cartridge to penetrate at least a layer of the adjacent layers of body tissue and to deliver electrosurgical energy to the body tissue during at least one of before, after and concomitant with firing of the surgical stapler.

The tissue cauterizing system includes a source of electrical energy electrically connected to the surgical stapler via a first and a second power line, and wherein the plurality of deployable needles have a first position wherein the plurality of deployable needles are entirely retained within the staple cartridge and a second position wherein the tip of each of the plurality of deployable needles projects from the staple cartridge.

The first jaw includes the driving member being adapted to be slidingly received within the staple cartridge, the driving member being adapted to displace each of the plurality of deployable needles from the first position to the second position.

The driving member includes an energy transmission strip, wherein the energy transmission strip is electrically connected to the first power line and electrically interconnects each of the plurality of deployable needles with the first power line. Each of the plurality of deployable needles and the transmission strip are made from an electrically conductive material. The staple anvil is electrically connected to the second power line.

It is envisioned that when the plurality of deployable needles is in the second position and the distal end of each of the plurality of deployable needles penetrates into tissue at the target staple site the tip of the plurality of needles do not contact the staple anvil. Preferably, each of the plurality of deployable needles is biased to the first position.

The tissue cauterizing system includes a plurality of springs disposed, one each, about each of the plurality of deployable needles to bias each of the plurality of deployable needles to the first position. The source of electrical energy is an electrosurgical generator.

According to a further aspect of the present disclosure, a surgical stapler including a first jaw and a second jaw having a staple anvil, in a distal end thereof is disclosed. The surgical stapler includes a staple cartridge selectively receivable in the first jaw, wherein the staple cartridge includes one or more laterally spaced apart rows of staple slots formed in an upper surface thereof, a plurality of surgical staples disposed, one each, within the staple slots, a plurality of staple pushers disposed, one each, within the staple slots in a position to push and eject each of the plurality of staples from the staple slots, and a plurality of deployable needles disposed within the staple cartridge, each of the plurality of deployable needles having a first position wherein the needle is entirely retained within the staple cartridge and a second position wherein a tip portion of the needle projects from the staple cartridge. The surgical stapler further includes a driving member operatively associated with the first jaw, the driving member being adapted to be slidingly received within the staple cartridge and to transform a linear displacement thereof into a concomitant transverse displacement of the plurality of staple pushers and of the plurality of deployable needles. The drive member includes an energy transmission strip extending longitudinally along the length thereof, and a source of electrical energy electrically connected to the surgical stapler. The source of electrical energy includes a first power line electrically connected to the staple anvil, and a second power line electrically connected to the transmission strip of the drive member and electrically communicable with each of the plurality of deployable needles as the driving member is displaced in a distal direction through the staple cartridge.

Each of the plurality of deployable needles and the transmission strip are made from an electrically conductive material. Accordingly, when each of the plurality of deployable needles is in the second position the tip of each of the plurality of deployable needles penetrates into tissue at the target staple site and does not contact the staple anvil. Preferably, each of the plurality of deployable needles is biased into the first position.

The tissue cauterizing system includes a plurality of springs disposed, one each, about each of the plurality of deployable needles to bias each of the plurality of deployable needles into the first position.

According to another aspect of the present disclosure, a surgical staple cartridge configured and adapted to be removably received within a surgical stapler is provided and includes a working surface, one or more laterally spaced apart rows of staple slots formed in the working surface, a plurality of surgical staples disposed, one each, within the staple slots for mechanically securing adjacent layers of body tissue to one another, and a tissue property enhancing system for enhancing one or more properties of body tissue to be repaired or joined by the surgical stapler, the tissue property enhancing system being configured and adapted to non-mechanically enhance the repaired or joined body tissue. The tissue property enhancing system includes a wound closer material dispensing system for dispensing an amount of surgically biocompatible wound closure material to a target staple site during at least one of prior to, after and concomitant with a firing of the surgical stapler to expel a plurality of staples loaded in the staple cartridge, the tissue property enhancing system comprising at least one reservoir disposed in the staple cartridge for containing the biocompatible wound closure material therein, a plurality of ducts formed in the staple cartridge, wherein the plurality of ducts extend from the at least one adhesive reservoir to the upper surface of the staple cartridge, and a plurality of deployable needles each having a tip, the needles being adapted and disposed in the cartridge and ducts such that their tips can be extended out of the working surface of the staple cartridge and penetrate at least a layer of the adjacent layers of body tissue and to allow the biocompatible wound closure material to be delivered along the exterior of the needles and to penetrate one or more layers of the body tissue.

The tissue property enhancing system is configured and adapted to deliver an amount of the biocompatible wound closure material to at least one of the adjacent layers of body tissue to adhere the adjacent layers of body tissue to one another. The tissue property enhancing system is configured and adapted to deliver an amount of biocompatible wound closure material between the adjacent layers of body tissue to adhere the adjacent layers of body tissue to one another.

The staple cartridge preferably includes a reservoir adapted to contain a quantity of the biocompatible wound closure material. Normally each of the plurality of deployable needles is biased into a retracted condition.

The body tissue property enhancing system is configured and adapted to deliver an amount of electrical energy to at least one of the adjacent layers of body tissue to cauterize the adjacent layers of body tissue to one another. The plurality of deployable needles are adapted to deliver an amount of electrical energy to at least one of the layers of body tissue to cauterize the same. Each of the plurality of deployable needles is biased to a retracted condition.

In a further aspect of the present disclosure, a surgical stapler is provided and includes a handle assembly, a tubular body portion extending from the handle assembly, a staple cartridge assembly operatively connected to a distal end of the tubular body, the staple cartridge including a pair of annular arrays of staple receiving slots, wherein each staple receiving slot includes a surgical staple disposed therein for mechanically securing adjacent layers of body tissue to one another, an anvil member operatively connected by a shaft to the distal end of the tubular body, opposite the staple cartridge assembly, and a body tissue property enhancing system configured and adapted to non-mechanically enhance the repairing or joining of the adjacent layers of body tissue to one another along an annular staple line formed by the firing of the surgical stapler, the body tissue property enhancing system including an annular array of needle receiving slots, and a plurality of deployable needles disposed, one each, in the annular array of needle receiving slots for delivering the body tissue enhancer.

The body tissue property reinforcing system is configured and adapted to deliver an amount of biocompatible wound closure material to the adjacent layers of body tissue to enhance the repairing or joining of the adjacent layers of body tissue to one another.

The biocompatible wound closure material is preferably an adhesive and the body tissue property enhancing system is configured and adapted to deliver an amount of the adhesive into at least one of the adjacent layers of body tissue to adhere the adjacent layers of body tissue to one another.

The surgical stapler is for performing an end-to-end anastomosis operation.

The staple cartridge assembly includes an staple pusher including a distal portion defining concentric rings of peripherally spaced fingers adapted to be receivable, one each, within a respective one of the pair of annular arrays of staple receiving slots and a respective one of the annular array of needle receiving slots. Each deployable needle is preferably biased into a retracted position, preferably by a spring.

The surgical stapler further includes a plurality of capsules disposed, one each, in the array of needle receiving slots, between a respective needle and a respective finger which is receivable in the needle receiving slot. Each capsule encapsulates a quantity of biocompatible wound closure material therein. Each capsule is adapted to rupture upon application of a compressive force. The compressive force is applied to each of the capsules by the distal advancement of the fingers receivable within the needle receiving slots and through the respective needle receiving slots.

It is envisioned that distal advancement of the fingers receivable within the needle receiving slots causes the plurality of needles to deploy.

The body tissue property reinforcing system is configured and adapted to deliver an amount of electrical energy to the adjacent layers of body tissue to cauterize the adjacent layers of body tissue to one another. The body tissue property enhancing system is preferably configured and adapted to deliver an amount of electrical energy to at least one of the adjacent layers of body tissue to cauterize the adjacent layers of body tissue to one another. It is contemplated that distal advancement of the fingers receivable within the needle receiving slots causes the plurality of needles to deploy.

The anvil member includes a plurality of contact pads disposed, one each, in juxtaposed axial alignment with each of the plurality of deployable needles. It is envisioned that each of the plurality of fingers receivable within the needle receiving slots, each of the plurality of needles and each of the contact pads are made from an electrically conductive material. Each of the plurality of fingers receivable within the needle receiving slots is electrically connected to a power line adapted to deliver electrical energy to the plurality of fingers receivable within the needle receiving slots.

Each of the plurality of contact pads are electrically connected to a power line adapted to at least one of deliver and dissipate electrical energy to and/or from each of the plurality of contact pads. Each of the plurality of fingers receivable within the needle receiving slots, each of the plurality of needles and each of the contact pads are electrically connected to a source of electrical energy.

It is an object of the present disclosure to provide surgical instruments which apply surgical staples and one biocompatible wound closure materials, for example, adhesives, sealants and hemostats and/or other enhancers, e.g., energy for cauterization, to enhance one or more properties of body tissue to be repaired or joined by the surgical staples.

It is another object of the present disclosure to provide the aforementioned surgical instruments which can be in the form of surgical staplers and cartridges and disposable loading units for surgical staplers.

It is another object of the present disclosure to provide a stapling device with a body tissue property enhancing system.

It is another object of the present disclosure to provide surgical instruments for stapling and enhancing the adhesion of the body tissue repaired or joined by the surgical staples.

It is yet another object of the present disclosure to provide surgical stapling instruments for reducing or preventing leakage of fluid where body tissue has been repaired and/or joined by staples.

It is yet another object of the present disclosure to provide surgical stapling instruments for reducing or preventing bleeding where the body tissue has been repaired and/or joined by the staples.

It is yet another object of the present disclosure to provide stapling devices electrocautery capabilities for stapling and welding and/or cauterizing tissue.

It is still another object of the present disclosure to provide surgical staplers that can employ staples in combination with biocompatible wound closure materials, e.g., adhesives and/or electrocautery to improve the staple/tissue holding strength, healing patterns, sealing, hemostasis and long term patency of the staple line.

It is a further object of the present disclosure to provide surgical staplers having fewer staples and mechanical components therein.

It is still a further object of the present disclosure to provide surgical staplers which are less expensive to manufacture, due to the reduced number of components, which require a reduced firing force and which allow a reduced criticality of manufacturing tolerances of some of the components of the surgical staplers.

BRIEF DESCRIPTION OF THE DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure.

FIG. 8 is an enlarged vertical cross-sectional view taken longitudinally through the cartridge assembly of the surgical stapler of FIG. 7 and illustrating a staple line reinforcing system in accordance with an embodiment of the present disclosure;

FIG. 9 is an enlarged partial sectional view taken along lines 9-9 of FIG. 8;

DETAILED DESCRIPTION OF PREFERRED EMBODIMENTS

Figure 1:
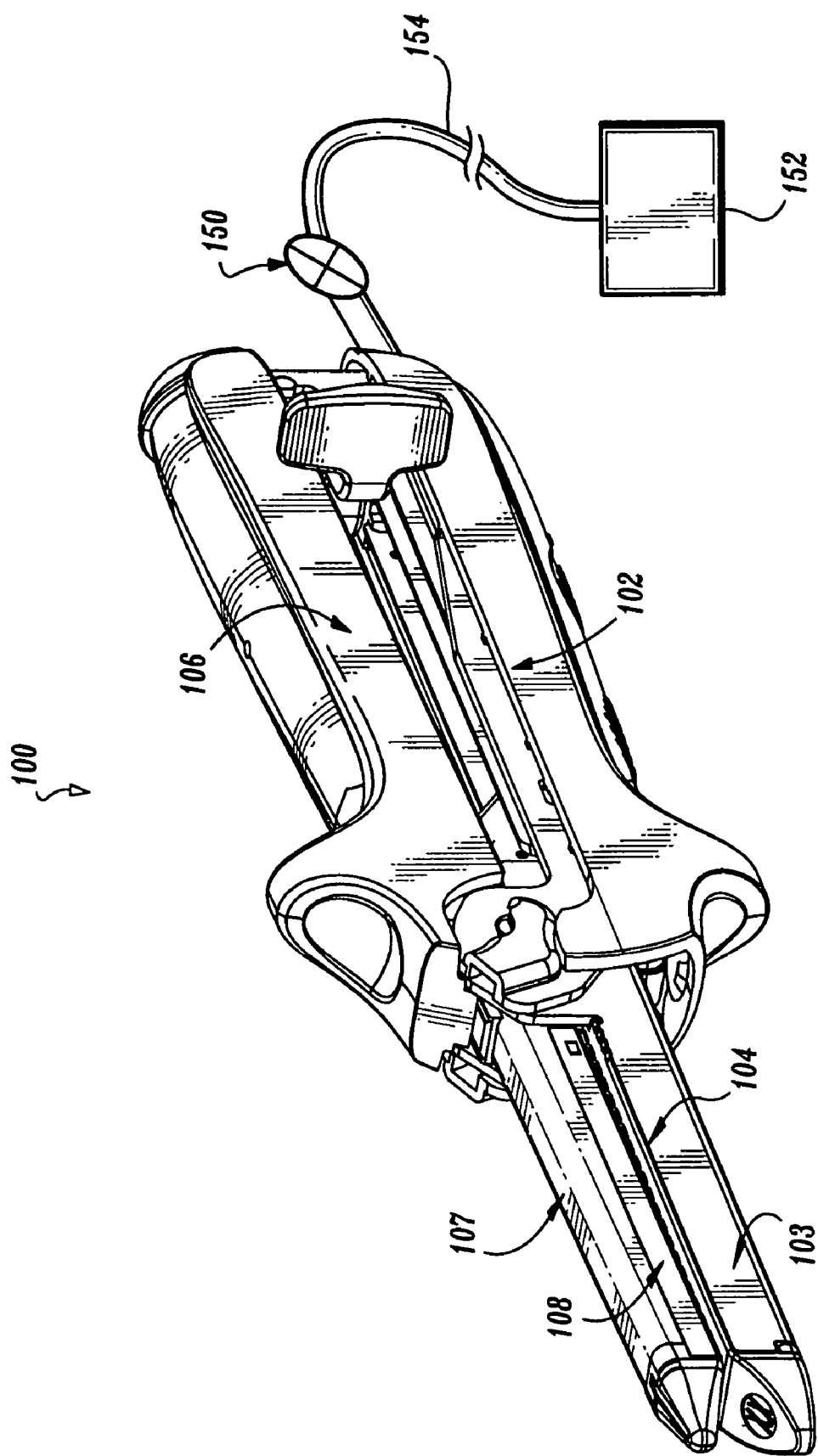
FIG. 1 is a perspective view of a surgical stapler in accordance with the present disclosure.

Preferred embodiments of the presently disclosed surgical stapler will now be described in detail with reference to the drawing figures wherein like reference numerals identify similar or identical elements. As used herein and as is traditional, the term "distal" refers to that portion which is further from the user while the term "proximal" refers to that portion which is closer to the user.

There are several known types of surgical staplers for various procedures with each stapler including a staple anvil and staple cartridge which are adjustably approximated relative to each other. A typical staple cartridge usually has at least two laterally spaced rows of staple slots and staples therein for mechanically joining adjacent layers of tissue to one another. The staple anvil likewise usually includes two rows of staple forming depressions formed therein which are aligned with the rows of staples slots in the cartridge. In use, each of the surgical staplers involves gripping tissue to be fastened between the staple cartridge and the staple anvil, ejecting individual staples, forcing the staples through the gripped tissue and into respective staple forming depressions and forming or closing the staples against the staple forming depressions thereby mechanically joining the adjacent layers of tissue to one another.

While the following description will generally relate to linear-type surgical staplers, it will be understood that the present disclosure applies to any of several known types of surgical staplers specifically adapted for use in various procedures, such as end-to-end anastomosis; circular end-to-end anastomosis; gastrointestinal anastomosis; endoscopic or laparoscopic gastrointestinal anastomosis and transverse anastomosis. Specific examples of staplers for these various procedures include but are not limited to, for example, EEA™, CEEA™, GIA™, EndoGIA™, and TA™ each of which are available from Tyco Healthcare Group, LP, Norwalk, Conn.

Figure 2:
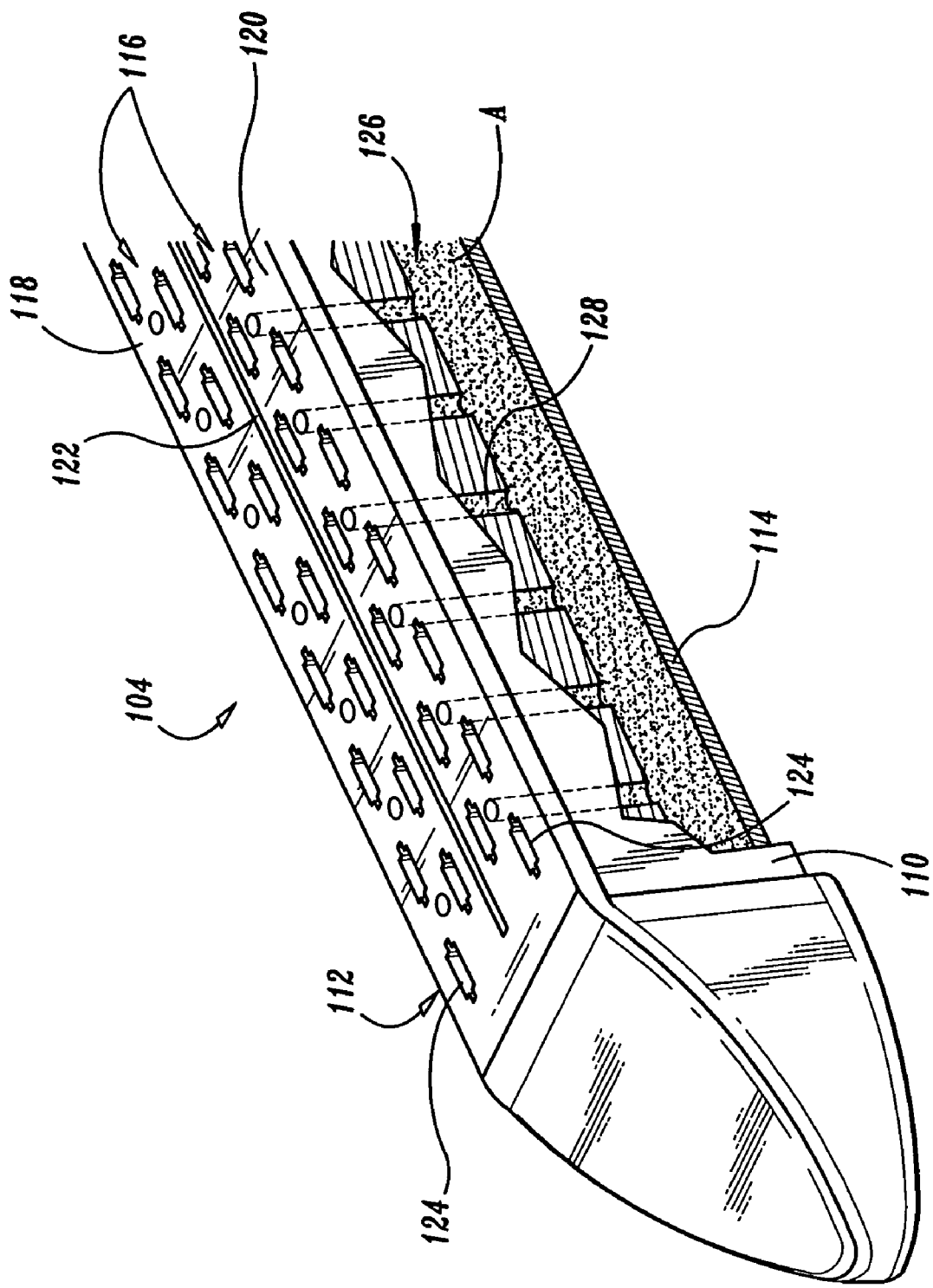
FIG. 2 is an enlarged partial perspective view, with portions broken away, of a distal end of a staple cartridge of the surgical stapler shown in FIG. 1.
Figure 3:
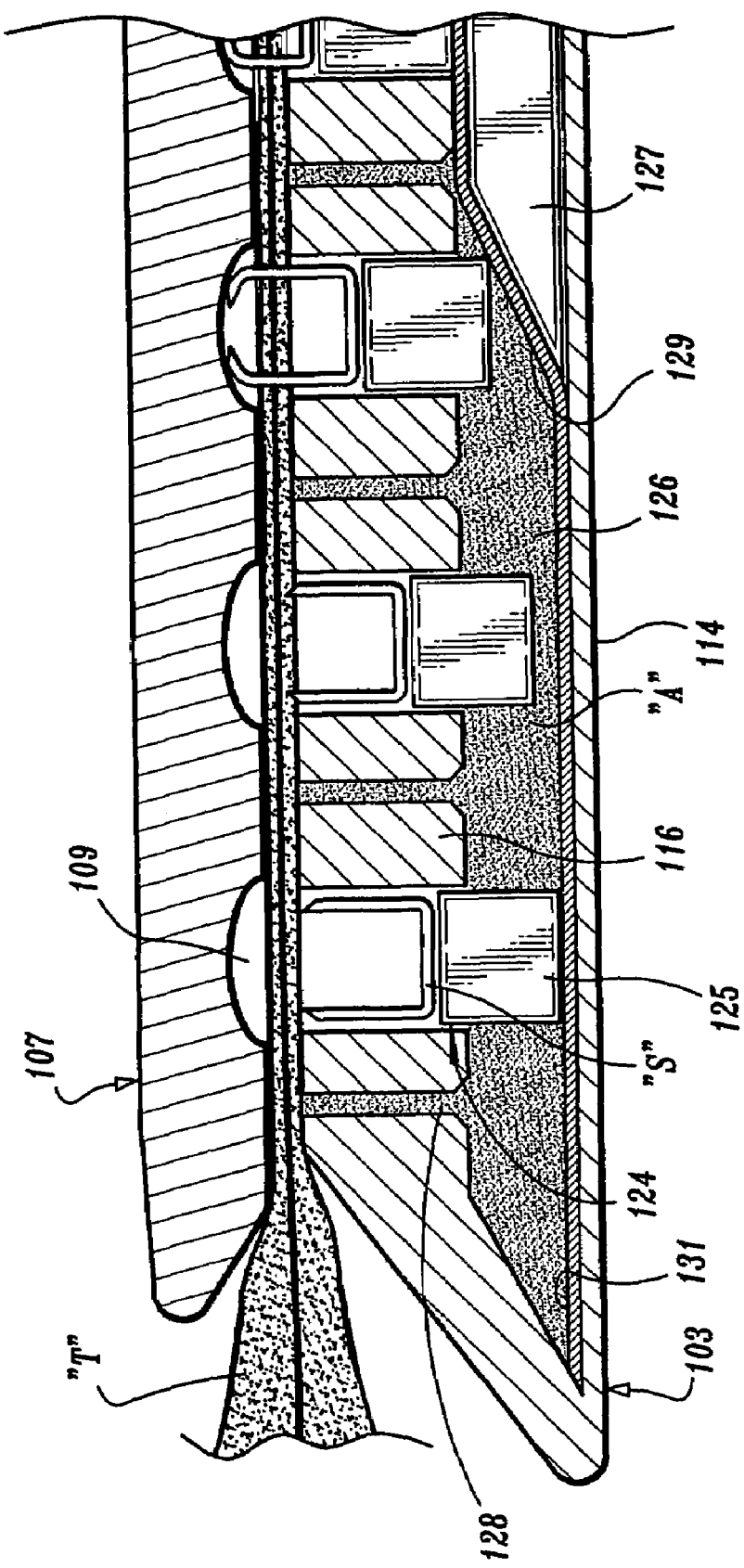
FIG. 3 is an enlarged longitudinal vertical cross-sectional schematic view, with portions in side elevation, of the distal end of the surgical stapler of FIG. 1 illustrating the firing thereof.
Figure 6:
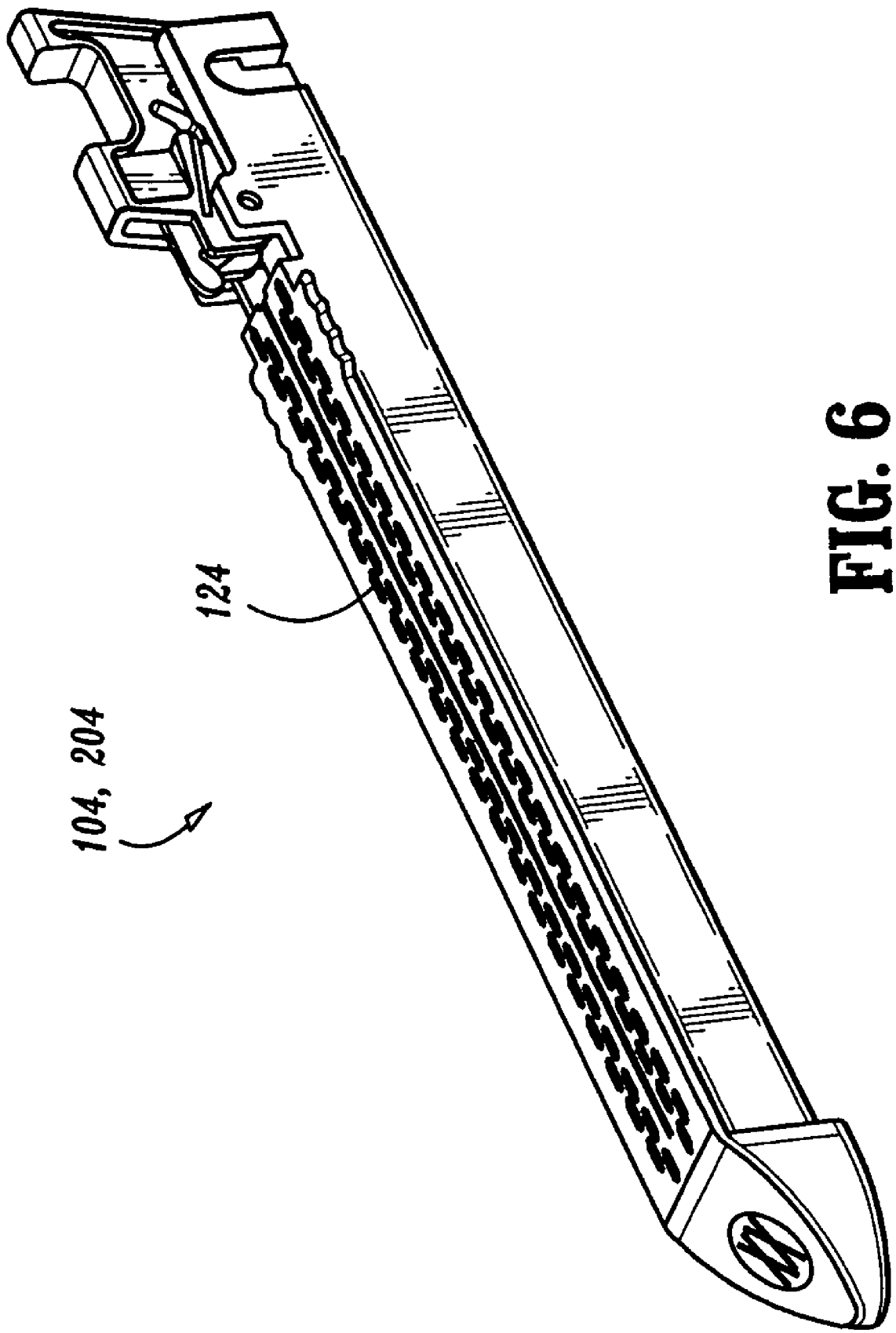
FIG. 6 is a perspective view of a removable staple cartridge in accordance with any one of the embodiments illustrated above.
Figure 7:
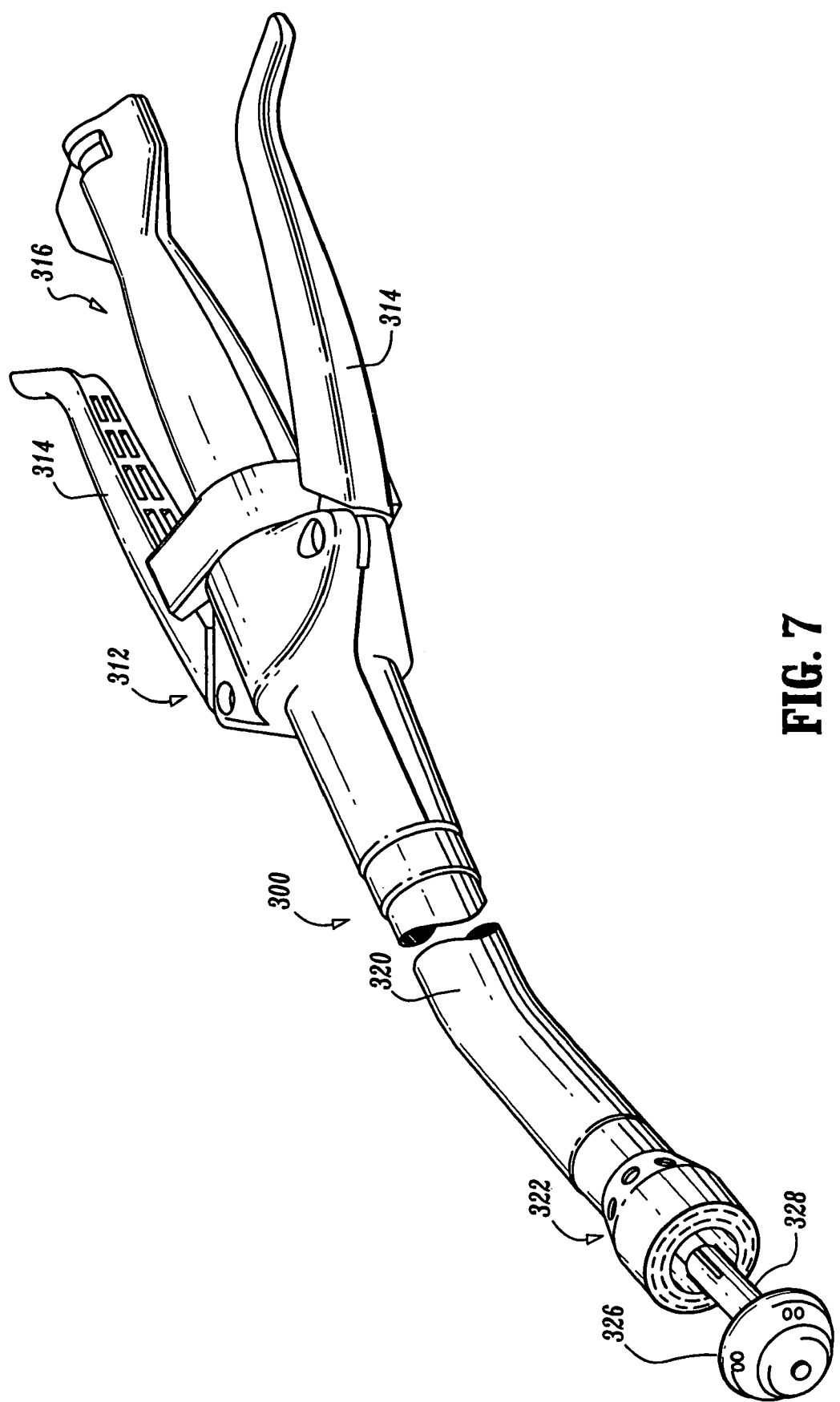
FIG. 7 is a perspective view of a surgical stapler in accordance with another embodiment of the present disclosure.

Referring now in detail to the drawings, FIGS. 1-3 show a surgical stapler generally designated as 100 in accordance with an embodiment of the present disclosure. Surgical stapler 100 includes a first handle 102 having a first jaw 103 configured and dimensioned to receive a replaceable staple cartridge 104 (e.g., a disposable loading unit or "DLU" as seen in FIG. 6) in a distal end thereof, and a second handle 106 having a second jaw 107 defining a staple anvil 108 formed in a distal end thereof, such that staple cartridge 104 is juxtaposed and substantially aligned with staple anvil 108.

FIG. 2 shows that staple cartridge 104 of surgical stapler 100 includes a pair of substantially parallel spaced apart side walls 110 and 112, a bottom wall 114 and a top wall 116. Preferably, top wall 116 is longitudinally divided into a pair of surface portions 118 and 120, respectively, by a knife track 122 extending therealong. Knife track 122 is configured and adapted to receive slidable cutting means (not shown) therein.

As seen in FIGS. 2 and 3, each surface portion 118 and 120 includes a pair of laterally spaced offset rows of staple slots 124 configured and adapted to retain a surgical staple "S" therein and extending substantially along a length, preferably the entire length thereof. While a pair of rows of staple slots 124 is preferred for each surface portion 118, 120, it is contemplated that any number of rows (e.g., one, three, etc.) can be provided depending on the instrument and the application. Staple cartridge 104 further includes a plurality of staple pushers 125, in this embodiment each slidably disposed beneath a staple "S" in a staple slot 124. A plurality of staple pushers can be joined into or as a unitary or integral structure, such that the structure can push or eject a plurality of staples "S" in, or from, a plurality of staple slots. First handle 102 of surgical stapler 100 further includes at least one drive member 127 slidingly receivable into staple cartridge 104. Drive member 127 includes an angled surface 129 which transforms a linear displacement of drive member 127 into a transverse displacement of staple pushers 125. In use, as drive member 127 is advanced distally, it acts like a cam to drive staple pushers 125, and in turn to expel staples "S" through respective staple slots 124, through tissue "T" and into staple forming depressions 109 of staple anvil 108.

Surgical stapler 100 includes a body tissue property enhancing system configured and adapted to enhance one or more properties of the body tissue to be repaired or joined by surgical staples fired into the body tissue. The body tissue property enhancing system can be or include a staple line surgical enhancing or reinforcing system (hereafter "reinforcing system") for non-mechanically reinforcing the repaired or joined tissue created by the mechanical fastening of staples "S". According to one embodiment, surgical stapler 100 includes a biocompatible wound closure material dispensing system for dispensing an amount of a surgically biocompatible wound closure material, e.g., adhesive, sealant or hemostat, to a target staple site either before, after and/or concomitantly with the expelling of staples "S". In one aspect of the disclosure, "biocompatible wound closure material dispensing system" includes side walls 110, 112, bottom wall 114 and top wall 116 of staple cartridge 104 which define at least one adhesive reservoir 126 extending longitudinally through staple cartridge 104. Adhesive reservoir 126 is configured and adapted to retain an amount of surgical biocompatible wound closure material, e.g., an adhesive, "A" therein. Staple cartridge 104 further includes a plurality of channels or ducts 128 formed along the cartridge and extending from reservoir 126 to surface portions 118, 120.

Accordingly, in use, as one or more drive or driving members 127 move distally through first jaw 103 or cartridge 104, and displace staple pushers 125 through staple slots 124, which in turn drive staples "S" through tissue "T", drive members 127 concomitantly force biocompatible wound closure material, e.g., adhesive, "A" from reservoir 126 through ducts 128 and into contact with tissue "T".

It is envisioned that an enclosure or container adapted for fit and function could be employed in the cartridge or cartridge reservoir 126 for containing the biocompatible wound closure material.

As seen in FIG. 3, it is further envisioned that an elongated flexible liner 131 can be disposed within reservoir 126 such that as drive member 127 is distally advanced through reservoir 126, liner 131 can ride up angled surface 129 of drive member 127 to thereby force biocompatible wound closure material "A" out through ducts 128. The liner can assist in driving or camming pushers 125 up the angular camming surface of drive member 127.

While a single adhesive reservoir 126 defined by walls of cartridge 104 or liner 131 has been shown and described in FIGS. 2 and 3, it is envisioned that a plurality of discrete adhesive reservoirs can be employed, for example, even one reservoir per duct 128 or set of adjacent ducts 128. Preferably, each reservoir is defined by a chamber, preferably a flexible chamber which is configured and adapted to contain or store or retain a quantity of adhesive "A" therein. In this manner, when the plurality of reservoirs (one shown) are compressed, upon distal movement of drive members 127, a quantity of biocompatible adhesive "A" is squeezed in series out of each of the plurality of liners.

One or more liners 131 can be shaped and tailored to provide the desired pressure at the right time to feed adhesive from the one or more liners and through the ducts. For example, an elongated and/or wide-bodied liner for a plurality of ducts, in the longitudinal and/or transverse direction(s), can be compartmentalized to provide a series of compartments whose interstitial walls can break or leak upon exceeding a certain desired or selected force imparted by drive member 127. Liners 131 can be of shorter height at its distal end than at its proximal end to accommodate or tend to equalize pressure or build up at the distal end of each liner as drive member 127 moves distally toward the distal end of cartridge 104. Liner 131 can be made of any suitable hermetic material or combination of materials.

Surgical stapler 100 effectively joins or fastens adjoining layers of tissue "T" to one another generally in two distinct manners. In the first manner, surgical stapler 100 applies a series of staples "S" to the layers of tissue "T" much like a conventional surgical stapler by driving staples "S" through adjacent layers of tissue "T" and into anvil pockets 109 of staple anvil 108, thereby mechanically forming the legs of staples "S" against anvil pockets 109 and repairing or joining the adjacent layers or edges of tissue "T" to one another. In the second manner, surgical stapler 100 applies a line or lines or a series of lines or drops or beads of biocompatible wound closure material, e.g., adhesive, "A" along a or the length of the staple array, row(s) of line(s) by expelling a quantity of biocompatible wound closure material "A" from reservoir 126, through ducts 128, to or into the adjacent tissue or layers or edges of tissue "T".

The rows of staples "S" provide the necessary mechanical retaining force to hold the adjacent tissue or layers or edges of tissue "T" secured to one another during the healing process while the application of biocompatible wound closure material, here, adhesive "A" fills the gaps about the legs of staples where they penetrate the tissue, and/or between aligned or adjacent staples "S" in or adjacent, along one or more arrays, lines or rows of staples "S", and provides additional non-mechanical enhancing properties to staples "S" and particularly to the stapled repaired or joined tissue. In addition, for example, by providing a line of adhesive "A", between two adjacent rows of staples "S", a third row of staples "S", generally associated with conventional surgical staplers, sometimes depending, e.g., on the application, may be eliminated thereby reducing the number of staples to be applied, the number of mechanical parts of the stapler, thereby reducing the overall cost of manufacture and assembly of the surgical stapler.

While spot or non-continuous adhesive application has been primarily disclosed, it is envisioned that a less interrupted or uninterrupted or continuous line or bead of biocompatible wound closure material, e.g., adhesive, "A" can be applied along a or the entire length of one or more rows of staples "S". If a continuous line of adhesive application is desired, it is envisioned that ducts 128 need to be closely spaced to one another or their ports elongated so that an individual application, e.g., spot of adhesive "A" joins with an adjacent application or spot of adhesive "A". Alternatively, a longitudinal duct (not shown) can be formed in the working surface of the cartridge along each side of knife track 122 (see FIG. 2) and oriented such that adhesive "A" is expelled between the layers or edges of tissues "T" following a cutting of the adjacent layers of tissues "T" by cutting means (e.g., a knife). Moreover, in lieu or in addition to a single line of biocompatible adhesive "A" per surface 118 and 120 as has been disclosed, it is envisioned that any suitable number of lines of adhesive "A" can be provided along respective surfaces 118 and 120.

A single series or line of ports 129 for applying adhesive "A" can be formed between adjacent rows of staples "S". However, if multiple lines of adhesive "A" are provided as in FIG. 2, the lines can be applied either inside of or outside of rows of staples "S". In addition, in surgical staplers not having a knife track 122 dividing top wall 116, the rows of staples "S" and the line(s) of adhesive "A" can alternate with one another, such that the rows of staple "S" can be outside of the lines of adhesive "A", or the lines of adhesive "A" can be outside of the rows of staples "S" or any combination thereof.

Figure 3A:
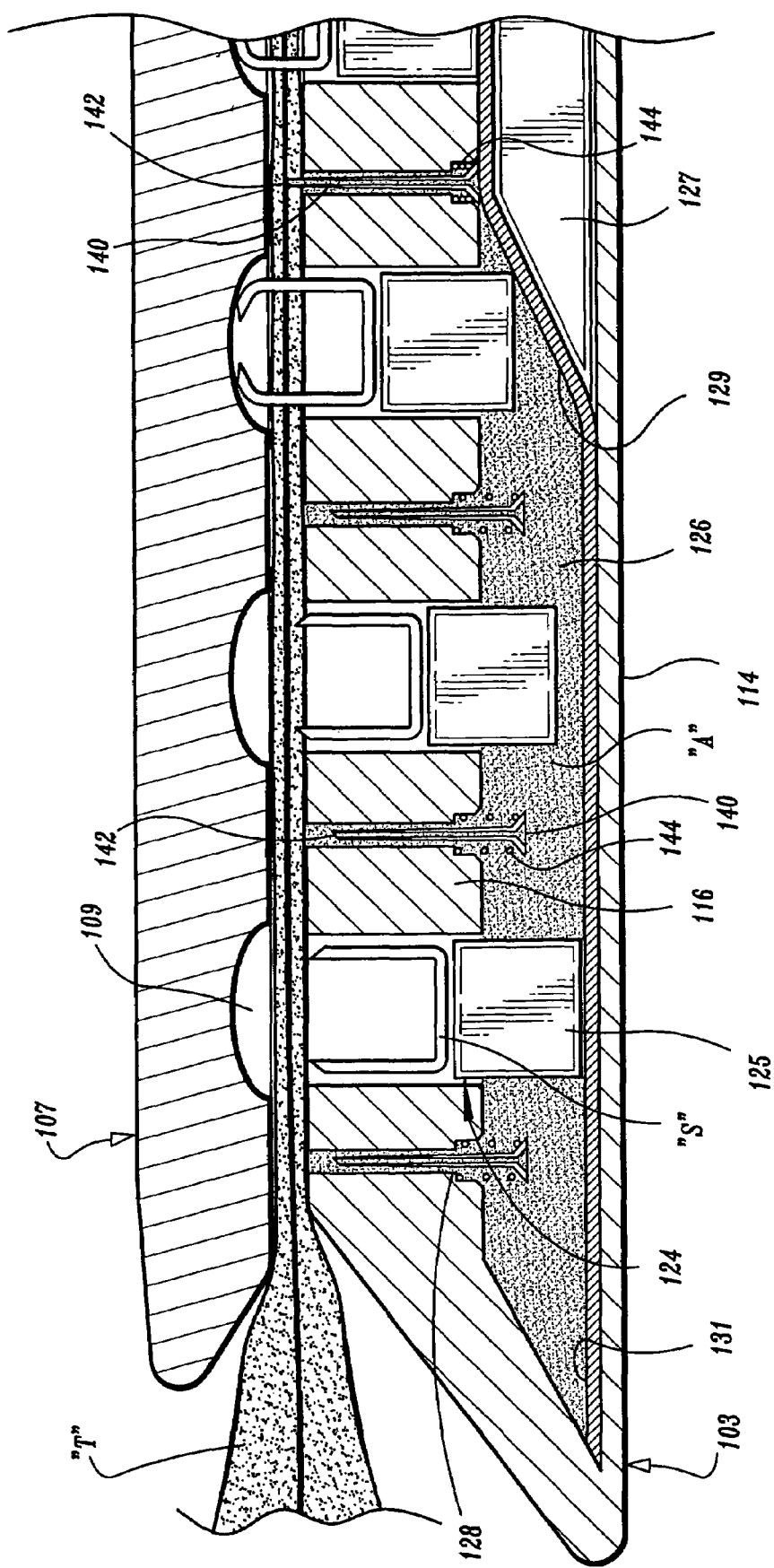
FIG. 3A is an enlarged longitudinal vertical cross-sectional schematic view, with portions in side elevation, of the distal end of a surgical stapler, according to an alternate embodiment of the present disclosure, illustrating the firing thereof.

Turning now to FIG. 3A, a distal end of a surgical stapler 100, according to an alternative embodiment of the present disclosure, is shown. As seen in FIG. 3A, surgical stapler 100 includes a deployable needle 140 operatively disposed within each duct 128'. Preferably, deployable needles 140 are configured and adapted to penetrate a layer of tissue "T" in order to deliver adhesive "A" between two adjacent layers of tissue "T". It is preferable that each drive member 127 is configured and adapted to act as a camming surface directly engaging the heads 140' of needles 140, or for indirectly engaging them through liner 131 to deploy needles 140, from ducts 128, through a first layer of body tissue "T" such that tip 142 of each needle 140 is located substantially between adjacent layers of tissue "T" and to expel a quantity of biocompatible adhesive "A" through each individual needle 140. The adhesive material need not be but preferably is expelled from needles 140 when tip 142 of needle 140 is activated or adjacent the adjoining tissue surfaces.

Accordingly, in use, as drive members 127 are moved distally through first jaw 103, drive members 127 sequentially transversely displace staple pushers 125 through respective staple slots 124, which in turn drives staples "S" through the layers of tissue "T". Concomitantly, drive members 127 sequentially deploy and drive needles 140 from ducts 128 in a manner such that tips 142 penetrate through a proximate-most layer of tissue "T", preferably, a distance such that tips 142 of needles 140 are positioned substantially between the adjoining surfaces of the layers of tissue "T" and to concomitantly expel or force adhesive "A" out through ducts 128 and needles 140 to the region between adjacent layers of tissue "T". Preferably, needles 140 are positioned such that needles 140 expel a quantity of biocompatible adhesive "A" at a location between successive staples "S" thereby filling the gaps which exist between adjacent staples "S". Alternatively, needle tips 142 can penetrate through each layer of tissue such that once needles 140 are withdrawn from tissue "T", adhesive "A" will remain or distribute itself in the space or hole formed by needle 140.

It is contemplated that needles 140 can be provided with withdrawing means operatively coupled thereto and configured and adapted to withdraw needles 140 into ducts 128 of staple cartridge 104 after biocompatible wound closure material, e.g., adhesive, "A" has been applied into, between or through the adjacent layers of tissue "T". For example, in another embodiment, drive members 127 can having a shaped, e.g., undulating, upper surface which rises and falls along a or the length thereof while each needle 140 can have a compression spring 144 disposed around it and, e.g., tacked at one end to top wall 116 and at its other end to head 140' to bias spring 144 in a direction which causes needle 140 to remain in contact with the surface of the drive member 127 in the manner of a cam follower. In this manner, needles 140 will rise and fall along with the profile of the upper surface of drive member 127 (i.e., deploy on distal movement and retract upon proximal movement). This feature is preferable so that the stapled tissue with adhesive material applied thereto can be easily separated from the jaws of the stapler and preferably also so that biocompatible adhesive "A" does not contact the surface of the surgical stapler or cause layers of tissue "T" to adhere to the surgical stapler.

While a fully self-contained surgical stapler 100 has been described relative to FIGS. 1-3A, it is contemplated and within the scope of the present disclosure that surgical stapler 100 can be provided with a fluid coupling member 150 (see FIG. 1) preferably extending from first handle 102, or from second handle 106 or from both handles 102 and 106. Coupling member 150 can be in fluid communication with reservoir 126 so that surgical stapler 100 can be fluidly coupled to a source of biocompatible adhesive 152, via a conduit (e.g., tube) 154. Accordingly, in use, biocompatible adhesive "A" can be applied to the target surgical site from remote source 152.

Surgical biocompatible wound closure materials which can be employed in or applied the surgical instruments, especially surgical staplers, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants which can be employed include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials which can be employed include fibrin-based, collagen-based, oxidized regenerated cellulose-based and gelatin-based topical hemostats. Examples of commercially available hemostat materials are fibrinogen-thrombin combination materials under sold the trade designations CoStasis™ by Tyco Healthcare Group, LP and Tisseel™ sold by Baxter International, Inc.

The biocompatible wound closure materials which can be employed with the surgical instruments, e.g., staplers disclosed herein preferably are non-toxic, capable of adhering to biological tissue, reaching stability quickly (e.g., typically within about 30 seconds to about 5 minutes), setting in wet conditions, and bonding to both biological tissue and synthetic materials, and provide sufficient strength to further stabilize the staple line. Biocompatible adhesives made up of proteinaceous materials and cross-linking agents have these characteristics. Biocompatible adhesives containing protein and a cross-linking agent are disclosed in U.S. Pat No. 5,385,606 to Kowanko, the entire disclosure of which is incorporated herein by reference.

While the above described embodiments relate generally to an open-type linear surgical stapler, endoscopic and laparoscopic linear type stapling instruments are also within the scope of the present disclosure. A typical endoscopic stapling apparatus includes a handle, an operative tool (i.e., an end effector) and an elongated shaft for interconnecting the operative tool to the handle. In general, the operative tool is designed to approximate and then to staple and divide tissue held therebetween. It is contemplated that the operative tool is a pair of opposed jaws including a staple anvil and a staple cartridge couplable, e.g., pivotally or transversely, to one another. Reference can be made to commonly assigned U.S. Pat. Nos. 6,330,965 and 6,241,139 to Milliman et al., the entire contents of which are incorporated herein by reference, for a more detailed explanation of the operation of surgical stapling apparatus 300 and of the approximation of the staple cartridge with the staple anvil.

Figure 4:
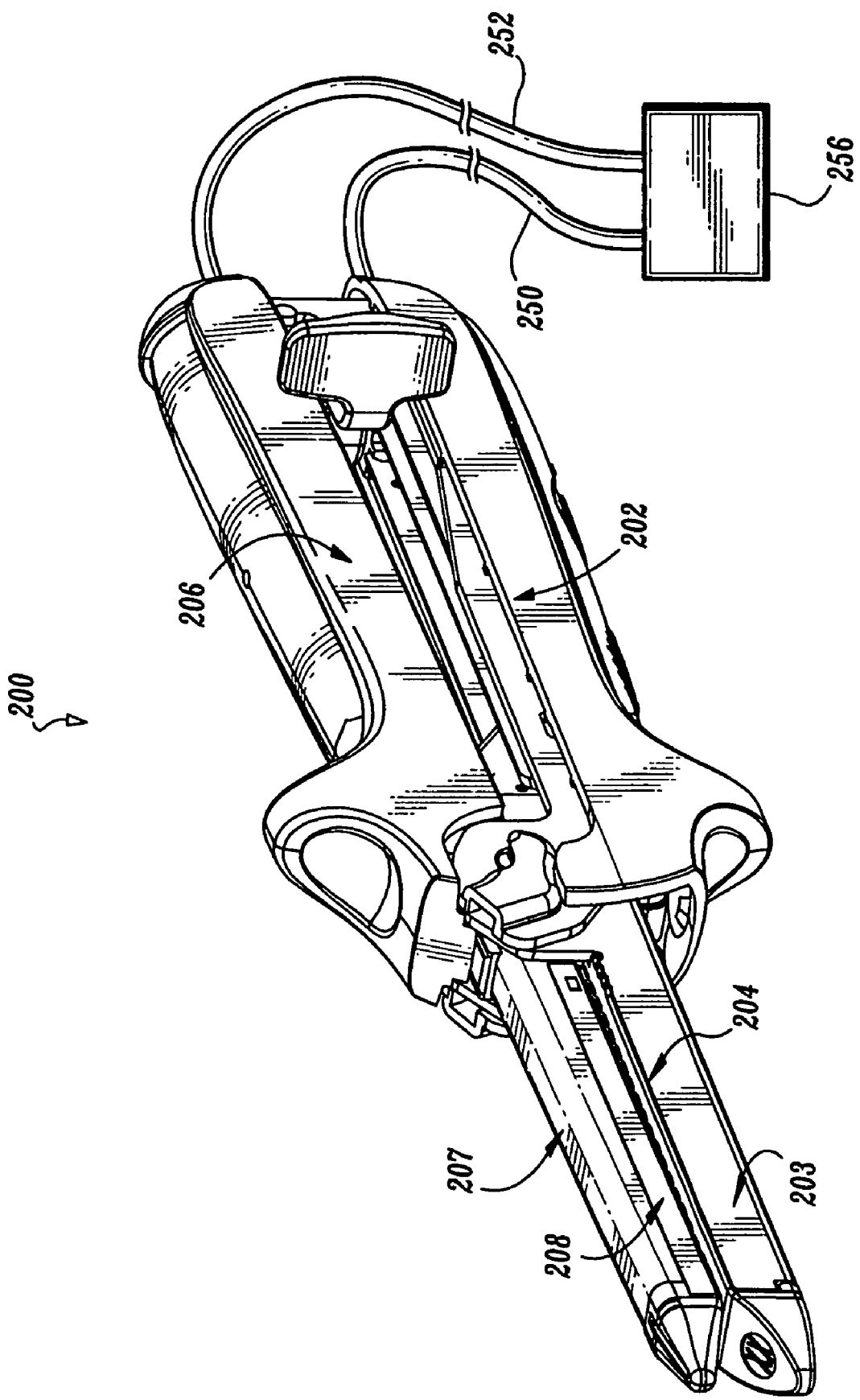
FIG. 4 is a perspective view of a surgical stapler in accordance with an alternative embodiment of the present disclosure.
Figure 5:
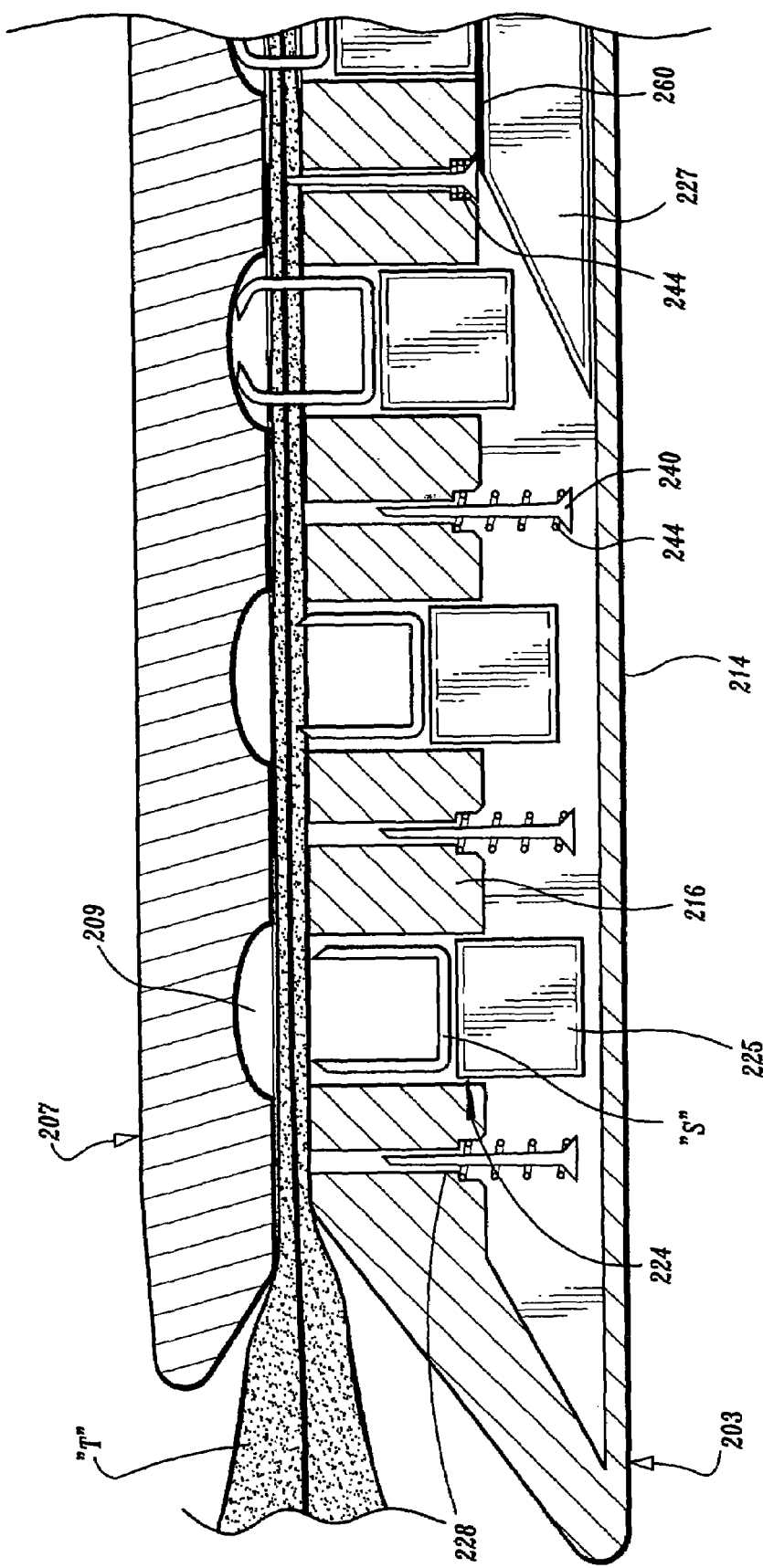
FIG. 5 is an enlarged longitudinal vertical cross-sectional schematic view, with portions is side elevation, of the distal end of the surgical stapler of FIG. 4.

In FIGS. 4 and 5, an alternative embodiment of a surgical stapler in accordance with the invention is shown generally as 200. Surgical stapler 200 includes a first handle 202 having a first jaw 203 configured and dimensioned to receive a staple cartridge 204 in a distal end thereof, and a second handle 206 having a second jaw 207 defining a staple anvil 208 formed in a distal end thereof, such that staple cartridge 204 is juxtaposed and substantially aligned with staple anvil 208.

Staple cartridge 204 of surgical stapler 200 includes a tissue property enhancing system for enhancing one or more properties of body tissue to be repaired or joined by a surgical stapler, the system being adapted to non-mechanically enhance the repaired or joined tissue. According to one embodiment, surgical stapler 200 includes a tissue cauterizing system for joining adjacent layers of body tissue to one another in a non-mechanical fashion during at least one of before, after or concomitant with a firing of surgical stapler 200 and to expel surgical staples "S" from staple cartridge 204. The tissue cauterizing system includes a source of electrical energy 256 (e.g., an electrosurgical generator) electrically connected to surgical stapler 200 via power lines 250, 252, and needles 240 operatively disposed within each duct 228 of staple cartridge 204. Preferably, first power line 250 extends proximally from first handle 202 and is in electrical contact with and provides a source of electrical energy and/or power to deployable needles 240 of staple cartridge 204.

Preferably, power line 250 is in electrical contact with first handle 202 and, more preferably, power line 250 is in electrical contact with an energy transmission strip 260 provided along an upper surface of drive member 227. Preferably, power line 252 is in electrical contact with second handle 206 and, more preferably, power line 252 is in electrical contact with anvil 208.

According to an embodiment of the present disclosure, first jaw 203, drive member 227 and staple pushers 225 are formed of a non-conductive or insulative material while needles 240 and transmission strip are formed of a conductive material. It is envisioned that anvil 208 of second jaw 207 is formed from a conductive material. Alternatively, anvil 208 can be formed of non-conductive or insulative material having areas or contact pads (not shown) disposed on the surface thereof which contact pads are formed from a conductive material. Preferably, a contact pad is in juxtaposition with a respective needle 240. Alternatively, if anvil 208 is made entirely of a conductive material, each anvil pocket 209 can be lined with a non-conductive or insulative material.

In use, first jaw 203 and second jaw 207 are positioned on either side of the surgical site where adjacent layers of tissue "T" are to be fastened to one another and cut in a manner such that staple cartridge 204 and staple anvil 208 are in juxtaposition. Surgical stapler 200 is then fired by moving drive member 227 distally, thereby driving staple pushers 225 into staples "S". This expels the legs of staples "S" through the adjacent layers of tissue "T" and against respective anvil depressions or pockets 209, thereby fully forming the staples and joining the layers of tissue "T" to one another.

Concomitantly with the expelling of staples "S" from staple cartridge 204, drive member 227 urges the ends of needles 240 through and beyond slots 228 into the adjacent layer(s) of tissue "T". Preferably, the tip of each needle 240 is blunt in order to inhibit the penetration of needle 240 fully through the adjacent layers of tissue "T" into contact with the surface of anvil 208. Preferably, each needle 240 is spring biased, by, for example, use of a compression spring 244 disposed about needles 240 and, for example, adhesively or otherwise secured at one end to wall 216 and at the other end to the head of needle 240. Springs 244 bring needles 240 into and maintain needles 240 in contact with strip 260 of drive member 227.

With the layers of adjacent tissue "T" held between first jaw 203 and second jaw 207 and needles 240 pressing into tissue "T", a user applies an RF energy to needles 240 from the source of energy 256. In particular, the RF energy travels from the source of energy 256, through power line 250, strip 260, needles 240, the adjacent layers of tissue "T", anvil 208 and out through power line 252. The RF energy is applied for a time and at a level sufficient to cauterize (i.e., spot weld) the adjacent layers of tissue "T" to one another.

After surgical stapler 200 has been fired, preferably drive member 227 is moved in a proximal direction, such that as the distal end of drive member 227 clears needles 240, and they are biasedly withdrawn back into staple cartridge 204 from the expression of springs 244. Alternatively, if drive member 227 cannot be moved in a proximal direction after the firing of staples, needles 240 can be removed from tissue "T" by disassociating first handle 202 from second handle 206.

Surgical stapler 200 effectively joins and/or fastens adjacent layers of tissue "T" to one another in two distinct manners. In the first manner, surgical stapler 200 conventionally applies a series of staples "S" to the adjacent layers of tissue "T" by driving staples "S" through the adjacent layers of tissue "T" and into anvil pockets 209 of staple anvil 208, thereby mechanically forming the legs of staples "S" against anvil pockets 209 and joining the adjacent layers of tissue "T" to one another. In the second manner, surgical stapler 200 forms a series of spot or line welds along a or the length of the staple line(s) by cauterizing the adjacent layers of tissue "T" to one another. Preferably, needles 240 are positioned such that needles 240 produce a spot weld at a location between or adjacent successive or adjacent staples "S" thereby filling gaps which exist between adjacent staples "S".

As seen in FIG. 6, surgical staplers 100, 200 can be provided with a removable surgical staple cartridge 104, 204, respectively, as shown in the form of a Disposable Loading Unit (hereinafter "DLU"). Preferably, the DLU can be configured and adapted to include the individual features of the tissue property enhancing systems disclosed herein or any combinations thereof. In this manner, a single surgical stapler 100 or 200 can be employed and reused while the DLU can be used and disposed of after each use and/or replaced with an unused DLU as needed during the surgical procedure. For example, DLU's, with or without a knife, having different numbers of rows of staples, varying length staples, varying length needles and different types of biocompatible wound closure materials can be employed. It is within the scope of this invention that the features of the staple cartridge 104, 204 are contemplated for DLU's for endoscopic and laparoscopic staplers, including endoscopic gastrointestinal and transverse anastomotic staplers.

The row of staples "S" provides the necessary retaining force to hold the adjacent layers of tissue "T" secured to one another during the healing process while the spot welds or lines fill the gaps between adjacent staples "S" in a particular row of staples "S". In addition, in certain applications, by providing a linear succession of spot or line welds between or adjacent the two rows of staples "S", a third row of staples generally associated with conventional surgical staplers can be eliminated, thereby reducing the number of mechanical parts and reducing the overall cost of manufacturing and assembling of the surgical stapler.

While the above described surgical staplers have been described in connection with a linear-type staplers, it is envisioned that the above disclosure can be used in connection with various other surgical staplers as disclosed above, such as, for example, circular-type staplers.

Thus, FIGS. 7-10 show an alternative embodiment in the form of an annular or circular-type surgical stapler, shown generally as 300. Surgical stapler 300 includes a handle assembly 312 having at least one pivotable actuating handle member 314, and further includes an advancing member 316. Extending from handle assembly 312, there is provided a tubular body portion 320 which may be constructed so as to have a curved shaped along its length. Tubular body portion 320 may also be straight and in other embodiments may be flexible to bend to any configuration. Body portion 320 terminates in a staple cartridge assembly 322 which is associated with a pair of annular arrays of staple receiving slots 336 including a staple 324 (see FIG. 8) disposed in each one of the staple receiving slots 336. Positioned opposite staple cartridge assembly 322 there is provided an anvil member 326 which is connected to a distal end portion of surgical stapler 300 by a shaft 328.

As seen in FIG. 8, staple cartridge assembly 322 fits concentrically within the distal end of tubular body portion 320. Staple cartridge assembly 322 includes a staple pusher 330 including a proximal portion 332 having a generally frusto-conical shape and a distal portion defining two concentric rings of peripherally spaced fingers 334, each one of which is received within a staple receiving slot 336. In one embodiment, it is envisioned that proximal portion 332 of staple pusher 330 is configured and adapted to be contacted by a distal end of a driver tube 338. Hence, upon advancing staple pusher 330 by advancing driver tube 338, fingers 334 will pass further into staple receiving slots 336 thereby pushing staples 324 contained therein axially outward.

As seen in FIG. 8, a knife 340 substantially in the form of an open cup with the rim thereof defining a knife edge 342 received within staple cartridge assembly 322 and mounted to a distal surface of staple pusher 330. Preferably, knife edge 342 is disposed radially inward of the pair of annular arrays of staples 324. Accordingly, as staple pusher 330 is advanced by advancing driver tube 338, knife 340 is also advanced axially outward.

In operation, surgical stapler 300 is positioned within a tubular organ in the body of the patient and the ends of the organ to be joined are positioned in a gap between staple cartridge assembly 322 and anvil member 326. As is conventional, the ends of the organ may be secured over anvil member 326 and staple cartridge assembly 322 by a purse string suture prior to approximation of anvil member 326 to staple cartridge assembly 322. In order to approximate anvil member.326 towards staple cartridge assembly 322, grip member 318 is rotated to draw anvil member 326 toward staple cartridge assembly 322 and into position against staple cartridge assembly 322. Once the proper distance is set between anvil member 326 and staple cartridge assembly 322, actuating handles 314 may be pivoted to drive staple pusher 330, and in turn staples 324 and annular knife 340, through the tissue and against anvil member 326 to thereby complete the anastomosis.

With continued reference to FIG. 8, staple cartridge assembly 322 includes a body tissue property enhancing system including at least one annular array, preferably two annular arrays, of deployable needles 350 positioned within needle receiving slots 352 formed in a distal end of staple cartridge assembly 322. Preferably, a needle 350 is disposed in each needle receiving slot 352. Preferably, each needle 350 is biased to a retracted position within its respective needle receiving slot 352 by a spring 354 positioned about each needle 350 and disposed between an inner distal surface 322a of staple cartridge assembly 322 and a flange 350a formed at the proximal end of each needle 350.

A quantity of biocompatible wound closure material is provided within each needle receiving slot 352, preferably at a location proximal of needle 350. Preferably, a plurality of rigid, semi-rigid or flexible containers, here preferably shown as semi-rigid or flexible capsules 356, containing biocompatible wound closure material can be provided, one each, within needle receiving slots 352, wherein each capsule 356 encapsulates and/or includes a quantity of biocompatible wound closure material retained therein. It is envisioned that the distal portion of staple pusher 330 further defines an additional ring of peripherally spaced fingers 358, each one of which is received within a respective needle receiving slot 352.

Figure 10:
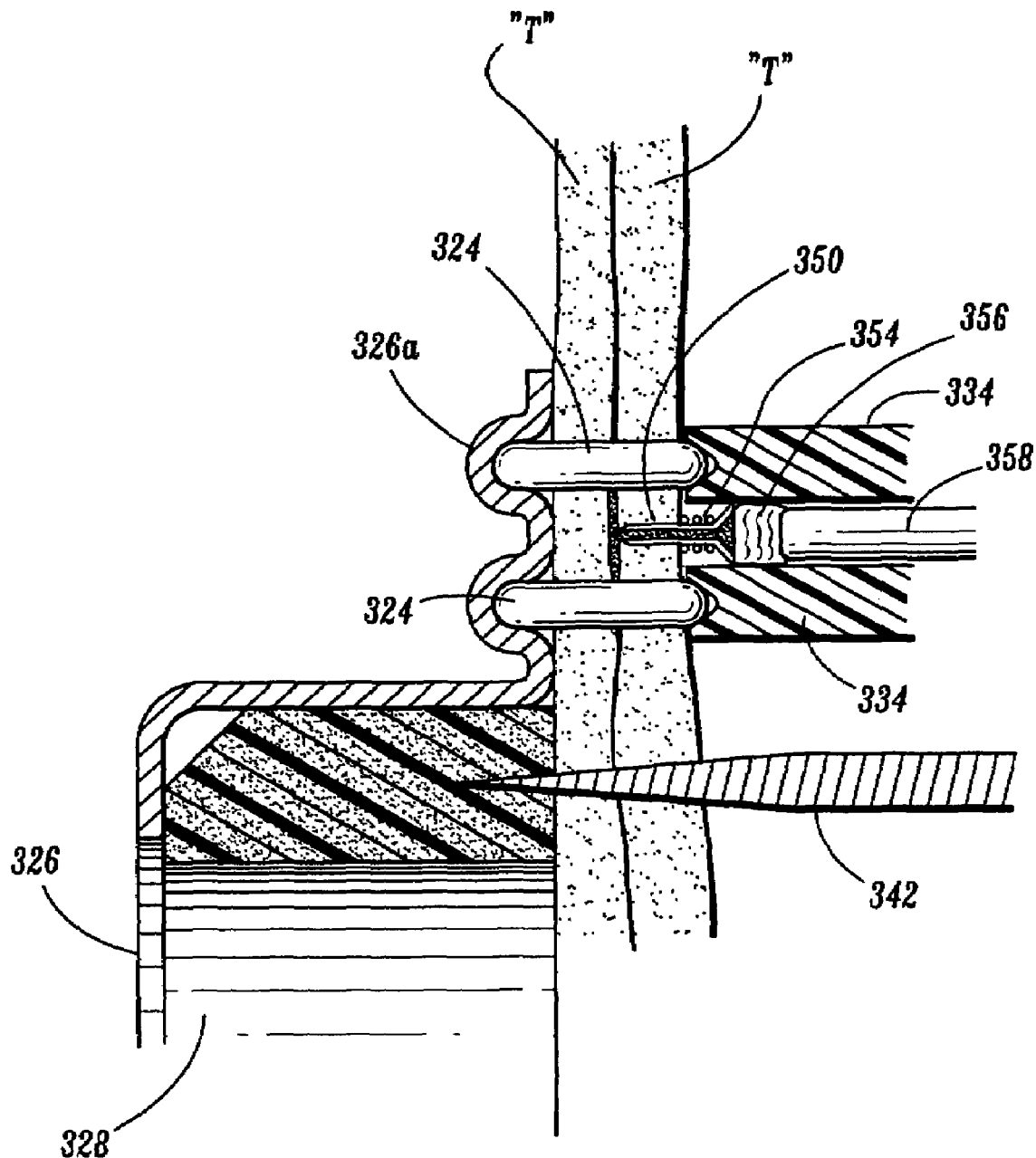
FIG. 10 is an enlarged view of the area indicated as 10 in FIG. 8.

In operation, upon advancing staple pusher 330, by advancing driver tube 338, fingers 358 will pass distally further into needle receiving slots 352 thereby pushing biocompatible wound closure material containing capsules 356 against the proximal end of needles 350 resulting in the deployment of needles 350 out of needle receiving slots 352. As seen in FIG. 10, needles 350 preferably penetrate at least one layer preferably both layers of tissue "T" clamped between staple cartridge assembly 322 and an anvil surface 326a of anvil member 326. Once needles 350 are fully deployed, as staple pusher 330 is advanced further, the compressive forces exerted on capsules 356 cause capsules 356 to rupture thereby dispensing biocompatible wound closure material into needle receiving slot 352. With capsules 356 ruptured, continued distal advancement of staple pusher 330 results in the expulsion of biocompatible wound closure material out through and/or about needles 350.

In this manner, the annular arrays of staples 324 provide the necessary retaining force to mechanically hold the adjacent layers of tissue "T" secured to one another during the healing process while a suitable biocompatible wound closure material fills the gaps between adjacent staples 324 in a particular annular array of staples 324.

Figure 11:
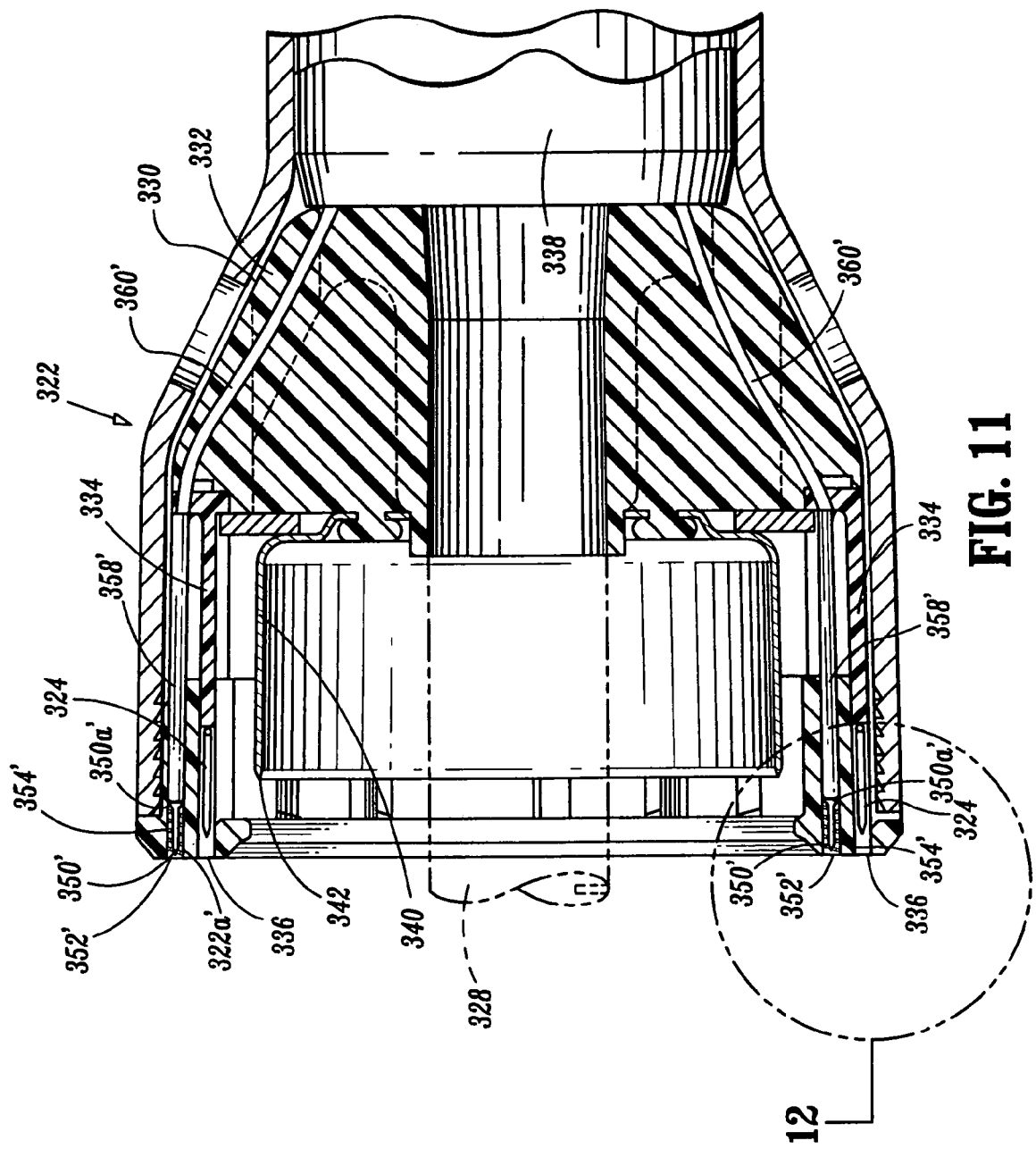
FIG. 11 is an enlarged vertical cross-sectional view taken longitudinally through the cartridge assembly of the surgical stapler of FIG. 7 and illustrating a staple line reinforcing system in accordance with another embodiment of the present disclosure.
Figure 12:
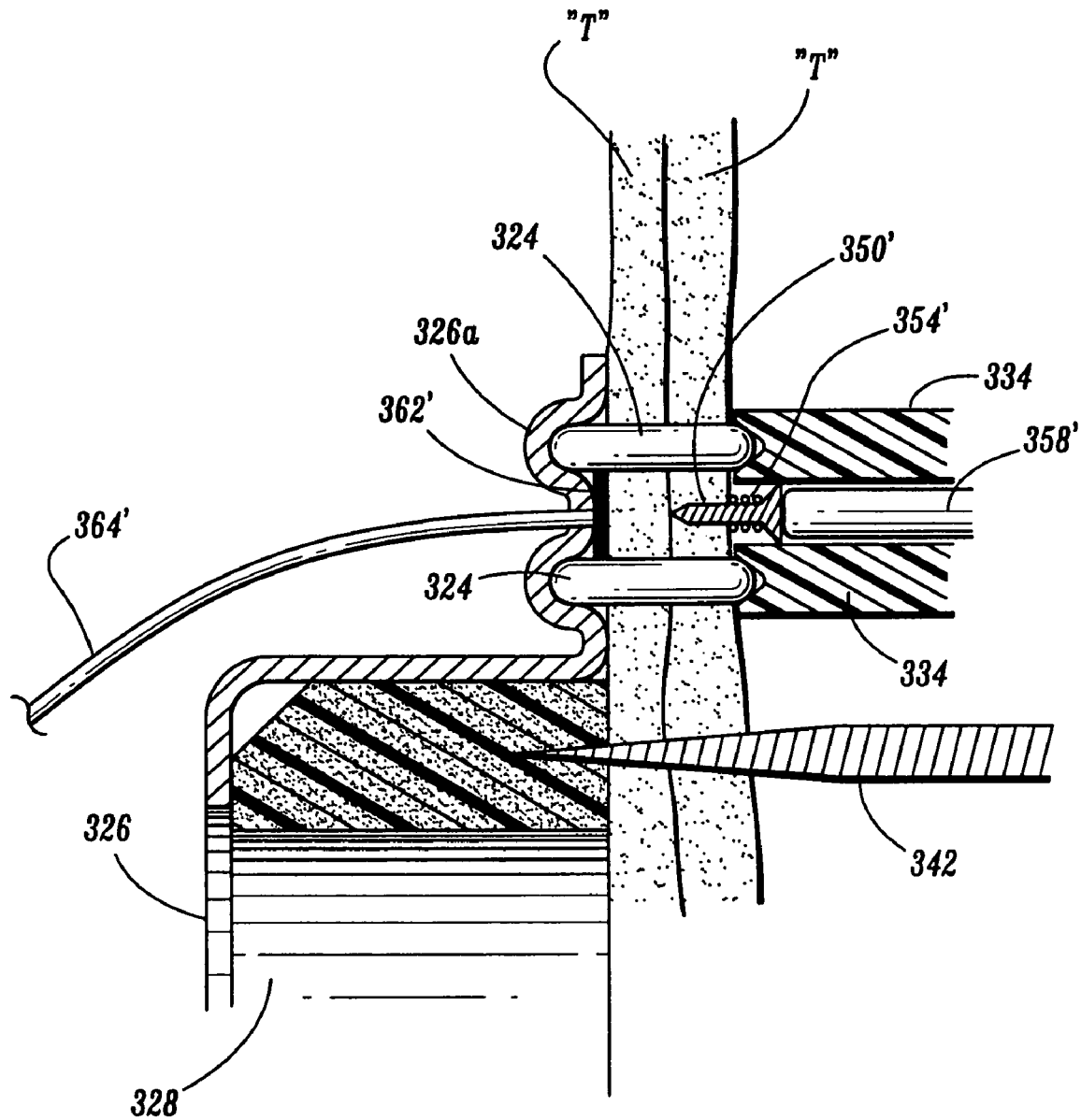
FIG. 12 is an enlarged view of the area indicated as 12 in FIG. 11.

Turning now to FIGS. 11 and 12, in another embodiment, staple cartridge assembly 320 includes a tissue property enhancement system including at least one annular array, preferably two annular arrays, of deployable needles 350' positioned within a corresponding needle receiving slot 352' formed in a distal end of staple cartridge assembly 322. Preferably, each needle 350' is biased to a retracted position within its respective needle receiving slot 352'. More preferably, each needle 350' is biased to the retracted position by a plurality of springs 354' positioned, one each, about needles 350' and disposed between an inner distal surface 322a of staple cartridge assembly 322 and a flange 350a' formed at the proximal end of each needle 350'. Preferably, needles 350' are made from an electrically conductive material.

The distal portion of staple pusher 330 further defines an additional ring of peripherally spaced fingers 358', each one of which is received within a respective needle receiving slot 352'. Preferably, fingers 358' are also made from an electrically conductive material. In this manner, when fingers 358' are in contact with needles 350', electrical energy can be transmitted from fingers 358' to needles 350'. It is envisioned that a proximal end of each finger 358' is in electrical contact with at least one power line 360' which extends through surgical stapler 300 and preferably to a source of electrical energy as described above.

In operation, upon advancing staple pusher 330, by advancing driver tube 338, fingers 358' will pass further into needle receiving slots 352' and in turn against the proximal end of needles 350' resulting in the deployment of needles 350' out of needle receiving slots 352'. As seen in FIG. 12, needles 350' preferably penetrate one layer of tissue "T" which is clamped between staple cartridge assembly 322 and an anvil surface 326a of anvil member 326. Once needles 350' are fully deployed, a suitable amount of electrical energy can be transmitted to needles 350' through power lines 360' and fingers 358' to cauterize and/or fuse adjacent layers of tissue "T" to one another. Preferably, as seen in FIG. 12, anvil surface 326a is provided with a plurality of electrical contact pads 362' positioned, one each, in juxtaposed axial alignment with needles 350'. Preferably, each contact pad 362' is in electrical contact with the source of electrical energy via at least one power line 364' extending from each contact pad 362', through anvil member 326, through shaft 328 and on to the source of electrical energy (i.e., source of electrical energy 256 from FIG. 4).

In this manner, the annular arrays of staples 324 provide the necessary retaining force to mechanically hold the adjacent layers of tissue "T" secured to one another during the healing process and the spot welds fill the gaps between adjacent staples 324 in a particular row of staples 324 and thereby enhance the holding force. In addition, by providing a succession of spot welds between the adjacent rows of staples 324, a third row of staples generally associated with conventional surgical staplers can be eliminated thereby reducing the number of mechanical parts and reducing the overall cost of manufacturing and assembly of the surgical stapler.

It will be understood that various modifications may be made to the embodiments of the presently disclosed surgical stapler. Therefore, the above description should not be construed as limiting, but merely as exemplifications of preferred embodiments. Those skilled in the art will envision other modifications within the scope and spirit of the present disclosure.

What is claimed is:

1. A method for enhancing one or more properties of body tissue to be repaired or joined by surgical staples comprising the steps of:
   providing a surgical stapler including a staple anvil and a staple cartridge each positioned adjacent a distal end of the surgical stapler and operable in juxtaposition relative to each other, the staple cartridge including:
      a working surface;
      one or more rows of individual staple slots formed in the working surface;
      a plurality of surgical staples individually disposed within the individual staple slots;
      a driving member for firing the surgical staples from their slots and against the staple anvil;
      a body tissue property enhancing system configured and adapted to enhance one or more properties of the body tissue to be repaired or joined by the surgical staples formed by firing them into body tissue, the body tissue property enhancing system including a reservoir of biocompatible wound closure material and a plurality of ducts in communication with the reservoir and the working surface of the cartridge; and
      a plurality of deployable needles each having a tip, the needles being adapted and disposed in the ducts such that the tips can be extended out of the working surface of the staple cartridge to penetrate at least a layer of adjacent layers of body tissue and to allow the biocompatible wound closure material to be delivered through the needles to penetrate one or more layers of body tissue;
   approximating the staple anvil and staple cartridge with adjacent layers of body tissue therebetween; and firing the surgical stapler, wherein firing of the surgical stapler includes driving the plurality of surgical staples through the adjacent layers of body tissue to mechanically secure the layers of body tissue together and concomitantly activating the body tissue enhancing system to enhance one or more properties of the adjacent layers of repaired or joined body tissue.

2. The method according to claim 1, wherein activating of the body tissue property enhancing system includes delivering an amount of the biocompatible wound closure material to at least one of or between the adjacent layers of repaired or joined body tissue.

3. The method according to claim 1, wherein upon firing of the surgical stapler, the biocompatible wound closure material is expelled from the reservoir of the staple cartridge.

4. The method according to claim 3, wherein in the providing step each of the plurality of deployable needles is normally biased to a non-extended position and is movable against the bias to the extended position.

5. The surgical stapler according to claim 1, wherein the plurality of deployable needles are each adapted to allow the biocompatible wound closure material to be delivered along an exterior of the needles.

6. The method according to claim 1, wherein the biocompatible wound closure material is an adhesive material.

7. The method according to claim 6, wherein the adhesive material is comprised of a protein derived, aldehyde based adhesive material.

8. The method according to claim 6, wherein the adhesive material is comprised of an albumin/glutaraldehyde material.

9. The method according to claim 6, wherein the adhesive material is a cyanoacrylate-based material.

10. The method according to claim 1, wherein the biocompatible wound closure material is a tissue sealant material.

11. The method according to claim 10, wherein the tissue sealant material is comprised of a synthetic polyethylene glycol-based hydrogel material.

12. The method according to claim 1, wherein the biocompatible wound closure material is a hemostat.

13. The method according to claim 12, wherein the hemostat is comprised of a combination of fibrinogen and thrombin.

14. A surgical stapler comprising:
   a first jaw adapted to receive a staple cartridge in a distal end of the first jaw, the staple cartridge containing a plurality of individual surgical staples, and having a working surface with a plurality of staple slots formed therein;
   a second jaw having a staple anvil in a distal end of the second jaw, such that during the operation of the surgical stapler the staple cartridge and the staple anvil can be approximated relative to one another;
   a driving member for firing the surgical staples from their staple slots and against the approximated staple anvil;
   a body tissue property enhancing system for enhancing one or more properties of body tissue to be repaired or joined by the surgical stapler, the body tissue property enhancing system including:
      a biocompatible wound closure material dispensing system for dispensing an amount of surgically biocompatible wound closure material to a target staple site during at least one of prior to, after and concomitant with a firing of the surgical stapler to expel the plurality of staples loaded in the staple cartridge, the body tissue property enhancing system comprising at least one reservoir disposed in the staple cartridge for containing the biocompatible wound closure material therein;
      a plurality of ducts formed in the staple cartridge, wherein the plurality of ducts communicate with and extend from the at least one adhesive reservoir to the working surface of the staple cartridge; and
      a plurality of deployable needles each having a tip, the needles being adapted and disposed in the ducts of the staple cartridge such that their tips can be extended out of the working surface of the staple cartridge to penetrate at least a layer of the adjacent layers of body tissue and to allow the biocompatible wound closure material to be delivered through the needles to penetrate one or more layers of the body tissue.

15. The surgical stapler according to claim 14, wherein the first jaw is adapted to receive a drive member being adapted to be slidingly disposed within the staple cartridge, the drive member being adapted to force the biocompatible wound closure material from the reservoir out through the plurality of ducts and about the needles disposed therein as the drive member is displaced in a distal direction, to allow the biocompatible wound closure material to penetrate into the body tissue to be repaired or joined.

16. The surgical stapler according to claim 15, wherein the staple cartridge further comprises: one or more laterally spaced rows of individual staple slots, the rows of staple slots extending along the staple cartridge; a plurality of individual surgical staples having a back span and disposed, one each, within the individual staple slots; and a plurality of staple pushers disposed one each within the staple slots and in a position to push one of the plurality of staples from the slot, wherein the drive member is adapted to displace the staple pushers into the slots and to concomitantly expel a quantity of the biocompatible wound closure material about the needles and out through the plurality of ducts.

17. The surgical stapler according to claim 15, wherein the biocompatible wound closure material dispensing system further includes a flexible liner extending longitudinally through the staple cartridge, wherein the liner prevents the biocompatible wound closure material from contacting the drive member as the drive member is displaced distally through the staple cartridge.

18. The surgical stapler according to claim 15, wherein the plurality of needles have a tip, a first position wherein the needles are entirely retained within the staple cartridge and a second position wherein the tips of the plurality of needles project out from the working surface of the staple cartridge.

19. The surgical stapler according to claim 18, wherein each of the plurality of needles is biased to the first position.

20. The surgical stapler according to claim 14, wherein the surgical stapler is for performing open gastrointestinal anastomosis operations.

21. The surgical stapler according to claim 14, wherein the surgical stapler is for performing endoscopic or laparoscopic gastrointestinal operations.

22. The surgical stapler according to claim 14, wherein the surgical stapler is for performing end-to-end anastomosis operations.

23. The surgical stapler according to claim 14, wherein the biocompatible wound closure material is an adhesive comprised of a protein derived, aldehyde-based adhesive material.

24. The surgical stapler according to claim 23, wherein the biocompatible wound closure material is an adhesive comprised of an albumin/glutaraldehyde material.

25. The surgical stapler according to claim 23, wherein the biocompatible wound closure material is an adhesive comprised of a cyanoacrylate-based material.

26. The surgical stapler according to claim 14, wherein the biocompatible wound closure material is a tissue sealant material.

27. The surgical stapler according to claim 26, wherein the tissue sealant material is comprised of a synthetic polyethylene glycol-based hydrogel material.

28. The surgical stapler according to claim 14, wherein the biocompatible wound closure material is a hemostat.

29. The surgical stapler according to claim 14, wherein the plurality of ducts are positioned adjacent to or aligned between the one or more laterally spaced apart rows of staple slots.

30. The surgical stapler according to claim 14, wherein each of the plurality of deployable needles is provided with a retracting element for withdrawing each of the plurality of deployable needles back into the staple cartridge after a firing of the surgical stapler.

31. A surgical staple cartridge configured and adapted to be removably received within a surgical stapler, the staple cartridge comprising:
a working surface;
one or more laterally spaced apart rows of staple slots formed in the working surface;
a plurality of surgical staples disposed, one each, within the staple slots for mechanically securing adjacent layers of body tissue to one another, and a tissue property enhancing system for enhancing one or more properties of body tissue to be repaired or joined by the surgical stapler, the tissue property enhancing system being configured and adapted to non-mechanically enhance the repaired or joined body tissue, the tissue property enhancing system including:
a wound closer material dispensing system for dispensing an amount of surgically biocompatible wound closure material to a target staple site during at least one of prior to, after and concomitant with a firing of the surgical stapler to expel a plurality of staples loaded in the staple cartridge, the tissue property enhancing system comprising at least one reservoir disposed in the staple cartridge for containing the biocompatible wound closure material therein;
a plurality of ducts formed in the staple cartridge, wherein the plurality of ducts extend from the at least one adhesive reservoir to the upper surface of the staple cartridge; and
a plurality of deployable needles each having a tip, the needles being adapted and disposed in the cartridge and ducts such that their tips can be extended out of the working surface of the staple cartridge and penetrate at least a layer of the adjacent layers of body tissue and to allow the biocompatible wound closure material to be delivered through the needles and to penetrate one or more layers of the body tissue.

32. The surgical staple cartridge according to claim 31, wherein the tissue property enhancing system is configured and adapted to deliver an amount of the biocompatible wound closure material to at least one of the adjacent layers of body tissue to adhere the adjacent layers of body tissue to one another.

33. The surgical staple cartridge according to claim 31, wherein the tissue property enhancing system is configured and adapted to deliver an amount of biocompatible wound closure material between the adjacent layers of body tissue to adhere the adjacent layers of body tissue to one another.

34. The surgical staple cartridge according to claim 31, wherein the staple cartridge includes a reservoir adapted to contain a quantity of the biocompatible wound closure material.

35. The surgical staple cartridge according to claim 34, wherein normally each of the plurality of deployable needles is biased into a retracted condition.

36. A surgical stapler comprising:
a handle assembly;
a tubular body portion extending from the handle assembly;
a staple cartridge assembly operatively connected to a distal end of the tubular body, the staple cartridge including a pair of annular arrays of staple receiving slots, wherein each staple receiving slot includes a surgical staple disposed therein for mechanically securing adjacent layers of body tissue to one another, an anvil member operatively connected by a shaft to the distal end of the tubular body, opposite the staple cartridge assembly; and
a body tissue property enhancing system configured and adapted to non-mechanically enhance one or more properties of the adjacent layers of repaired or joined body tissue to one another along an annular staple line formed by the firing of the surgical stapler, the body tissue property enhancing system including an annular array of needle receiving slots, and a plurality of deployable needles disposed, one each, in the annular array of needle receiving slots for delivering the body tissue enhancer.

37. The surgical stapler according to claim 36, wherein the body tissue property reinforcing system is configured and adapted to deliver an amount of biocompatible wound closure material to the adjacent layers of body tissue to enhance the repairing or joining of the adjacent layers of body tissue to one another.

38. The surgical stapler according to claim 36, wherein the biocompatible wound closure material is an adhesive and the body tissue property enhancing system is configured and adapted to deliver an amount of the adhesive into at least one of the adjacent layers of body tissue to adhere the adjacent layers of body tissue to one another.

39. The surgical stapler according to claim 36, wherein the surgical stapler is for performing end-to-end anastomosis operations.

40. The surgical stapler according to claim 39, wherein the staple cartridge assembly includes an staple pusher including a distal portion defining concentric rings of peripherally spaced fingers adapted to be receivable, one each, within a respective one of the pair of annular arrays of staple receiving slots and a respective one of the annular array of needle receiving slots.

41. The surgical stapler according to claim 40, wherein each deployable needle is biased into a retracted position.

42. The surgical stapler according to claim 40, wherein each deployable needle is biased to a retracted position by a spring.

43. The surgical stapler according to claim 42, further including a plurality of capsules disposed, one each, in the array of needle receiving slots, between a respective needle and a respective finger which is receivable in the needle receiving slot.

44. The surgical stapler according to claim 43, wherein each capsule encapsulates a quantity of biocompatible wound closure material therein.

45. The surgical stapler according to claim 44, wherein each capsule is adapted to rupture upon application of a compressive force.

46. The surgical stapler according to claim 45, wherein the compressive force is applied to each of the capsules by the distal advancement of the fingers receivable within the needle receiving slots and through the respective needle receiving slots.

47. The surgical stapler according to claim 46, wherein distal advancement of the fingers receivable within the needle receiving slots causes the plurality of needles to deploy.

* * * * *

UNITED STATES PATENT AND TRADEMARK OFFICE
CERTIFICATE OF CORRECTION

PATENT NO. : 7,517,356 B2
APPLICATION NO. : 10/510451
DATED : April 14, 2009
INVENTOR(S) : Russell Heinrich It is certified that error appears in the above-identified patent and that said Letters Patent is hereby corrected as shown below:

Column 19, line 49, claim 1 after the word "tissue", insert the word --property--;

Column 19, line 52, claim 2 cancel the word "of";

Column 19, line 60, claim 4 "wherein" should be changed to --wherein,--;

Column 19, line 61, claim 4 "step" should be changed to --step,--;

Column 19, line 64, claim 5 "surgical stapler" should be changed to --method--;

Column 20, line 60, claim 15 cancel the text "first jaw member is adapted to receive a drive member being" and insert the following text --driving member is--;

Column 20, line 61, claim 15 "drive" should be changed to --driving--;

Column 20, line 64, claim 15 "drive" should be changed to --driving--;

Column 21, line 9, claim 16 "drive" should be changed to --driving--;

Column 21, line 18, claim 17 "drive" first occurrence should be changed to --driving--;

Column 21, line 18, claim 17 "drive" second occurrence should be changed to --driving--;

Column 23, line 5, claim 36 after the word "enhancer", insert the following text --through the needles--;

UNITED STATES PATENT AND TRADEMARK OFFICE
CERTIFICATE OF CORRECTION

PATENT NO. : 7,517,356 B2
APPLICATION NO. : 10/510451
DATED : April 14, 2009
INVENTOR(S) : Russell Heinrich It is certified that error appears in the above-identified patent and that said Letters Patent is hereby corrected as shown below:

Column 23, line 7, claim 37 "reinforcing" should be changed to --enhancing--; and Column 23, line 22, claim 40 "an" should be changed to --a--.

Signed and Sealed this

Twenty-second Day of September, 2009

David J. Kappos
*Director of the United States Patent and Trademark Office*